US010231531B2

(12) United States Patent
Witchell et al.

(10) Patent No.: US 10,231,531 B2
(45) Date of Patent: Mar. 19, 2019

(54) SYSTEM, METHOD AND DEVICE FOR ANALYSIS OF HAIR AND SKIN AND PROVIDING FORMULATED HAIR AND SKIN PRODUCTS

(71) Applicant: Colorculture Network, LLC, Newtown, PA (US)

(72) Inventors: David J. Witchell, Newtown, PA (US); Erlend Olson, Newport Beach, CA (US)

(73) Assignee: Colorculture Network, LLC, Newtown, NY (US)

( * ) Notice: Subject to any disclaimer, the term of this patent is extended or adjusted under 35 U.S.C. 154(b) by 0 days.

(21) Appl. No.: 14/932,841

(22) Filed: Nov. 4, 2015

(65) Prior Publication Data

US 2017/0119130 A1    May 4, 2017

(51) Int. Cl.
*A45D 44/00* (2006.01)
*G01N 21/39* (2006.01)

(52) U.S. Cl.
CPC .......... *A45D 44/005* (2013.01); *G01N 21/39* (2013.01); *A45D 2044/007* (2013.01); *G01N 2201/06113* (2013.01); *G01N 2201/127* (2013.01)

(58) Field of Classification Search
None
See application file for complete search history.

(56) References Cited

U.S. PATENT DOCUMENTS

| | | | |
|---|---|---|---|
| 5,311,293 A | 5/1994 | MacFarlan et al. | |
| 5,313,267 A | 5/1994 | MacFarlane et al. | |
| 6,067,504 A | 5/2000 | MacFarlane et al. | |
| 6,157,445 A | 12/2000 | Macfarlane et al. | |
| 6,314,372 B1 | 11/2001 | Macfarlane et al. | |
| 6,985,230 B2 | 1/2006 | De Rigal et al. | |
| 7,151,851 B2 | 12/2006 | Ladjevardi | |
| 7,304,739 B2 | 12/2007 | Grossinger | |

(Continued)

FOREIGN PATENT DOCUMENTS

| | | |
|---|---|---|
| EP | 1428168 | 2/2010 |
| WO | WO2006044562 | 4/2006 |

(Continued)

OTHER PUBLICATIONS

Hyperspectral imaging system for in-vivo quantification of skin pigments, by Seroul et al., IFSCC, Oct. 2014, Paris France (Year: 2014).*

(Continued)

*Primary Examiner* — Vikkram Bali
(74) *Attorney, Agent, or Firm* — Frank J. Bonini, Jr.; John F. A. Earley, III; Harding, Earley, Follmer, Frailey, P.C.

(57) ABSTRACT

A method, system and device for determining the properties of hair and skin. The method, system and device facilities the selection and application of an application of a product to the hair or skin of an individual to achieve a desired target result. The hair or skin properties measured may include the hair composition and chemical components of the hair, as well as substances that may coat the hair, and other substances on, absorbed or absorbed on or into the hair. A hyper-spectral imaging component is employed to obtain information from the hair or skin and that information is used to provide a produce used to produce the target result.

34 Claims, 8 Drawing Sheets

(56) References Cited

U.S. PATENT DOCUMENTS

| | | |
|---|---|---|
| 7,463,356 B2 | 12/2008 | Grossinger et al. |
| 7,489,816 B2 | 2/2009 | Ladjevardi |
| 8,752,441 B2 | 6/2014 | Asaoka |
| 8,977,389 B2 | 3/2015 | Witchell et al. |
| 2003/0123056 A1 | 7/2003 | Barnes et al. |
| 2005/0036677 A1* | 2/2005 | Ladjevardi ............ G01N 21/84 382/162 |
| 2005/0213089 A1 | 9/2005 | Margalith et al. |
| 2005/0270528 A1 | 12/2005 | Geshwind et al. |
| 2005/0279915 A1* | 12/2005 | Elofson ................. C09K 11/02 250/205 |
| 2006/0085274 A1 | 4/2006 | Sottery et al. |
| 2006/0195300 A1* | 8/2006 | Grossinger .......... A45D 44/005 702/190 |
| 2011/0176029 A1 | 7/2011 | Boydston et al. |
| 2012/0075331 A1* | 3/2012 | Mallick ................ G06T 11/001 345/594 |
| 2013/0137961 A1 | 5/2013 | Barnes et al. |
| 2014/0082854 A1 | 3/2014 | Landa et al. |
| 2014/0118521 A1 | 5/2014 | Conti et al. |
| 2014/0293277 A1 | 10/2014 | Subbiah et al. |
| 2015/0089751 A1* | 4/2015 | Landa ................. B65D 1/0223 8/406 |
| 2017/0038297 A1* | 2/2017 | Miklatzky .............. G01N 21/47 |
| 2017/0178220 A1* | 6/2017 | Chong ............... G06Q 30/0631 |

FOREIGN PATENT DOCUMENTS

| | | |
|---|---|---|
| WO | WO2006107673 A2 | 10/2006 |
| WO | WO2006107673 A3 | 10/2006 |
| WO | WO2007026340 A2 | 3/2007 |
| WO | WO2007026340 A3 | 3/2007 |
| WO | WO2009152033 | 12/2009 |
| WO | WO2011071713 | 6/2011 |
| WO | WO2012127429 | 9/2012 |
| WO | WO2015044944 | 2/2015 |

OTHER PUBLICATIONS

Cullen, P., Edelman, G. J., Van Leeuwen, T. G. , Aalders, M. C. , Gaston, E. Hyperspectral Imaging for Non-Contact Analysis of Forensic Traces. Forensic Science International, Oct. 22, 2012.

Bedard, Noah; Hagen, Nathan; Gao, Liang; and Tkaczyk, Tomasz S.; Image mapping spectrometry: calibration and characterization; 2012 Society of Photo-Optical Instrumentation Engineers (SPIE); Opt Eng. Author manuscript; available in PMC Nov. 1, 2012.

Ames, Bruce N.; Kammen, H.O.; and Yamasaki, Edith; Hair Dyes Are Mutagenic: Identification of a Variety of Mutagenic Ingredients; Proc. Nat. Acad. Sci. USA, vol. 72, No. 6, pp. 2423-2427, Jun. 1975.

Brauns, Eric B.; and Dyer, R. Brian; Fourier Transform Hyperspectral Visible Imaging and the Nondestructive Analysis of Potentially Fraudulent Documents; Applied Spectroscopy; vol. 60, No. 8, 2006.

Hair dye 'CSI' could help police solve crimes (Feb. 18, 2015) retrieved Sep. 10, 2015 from http://phys.org/news/2015-02-hair-dye-csi-police-crimes.html.

* cited by examiner

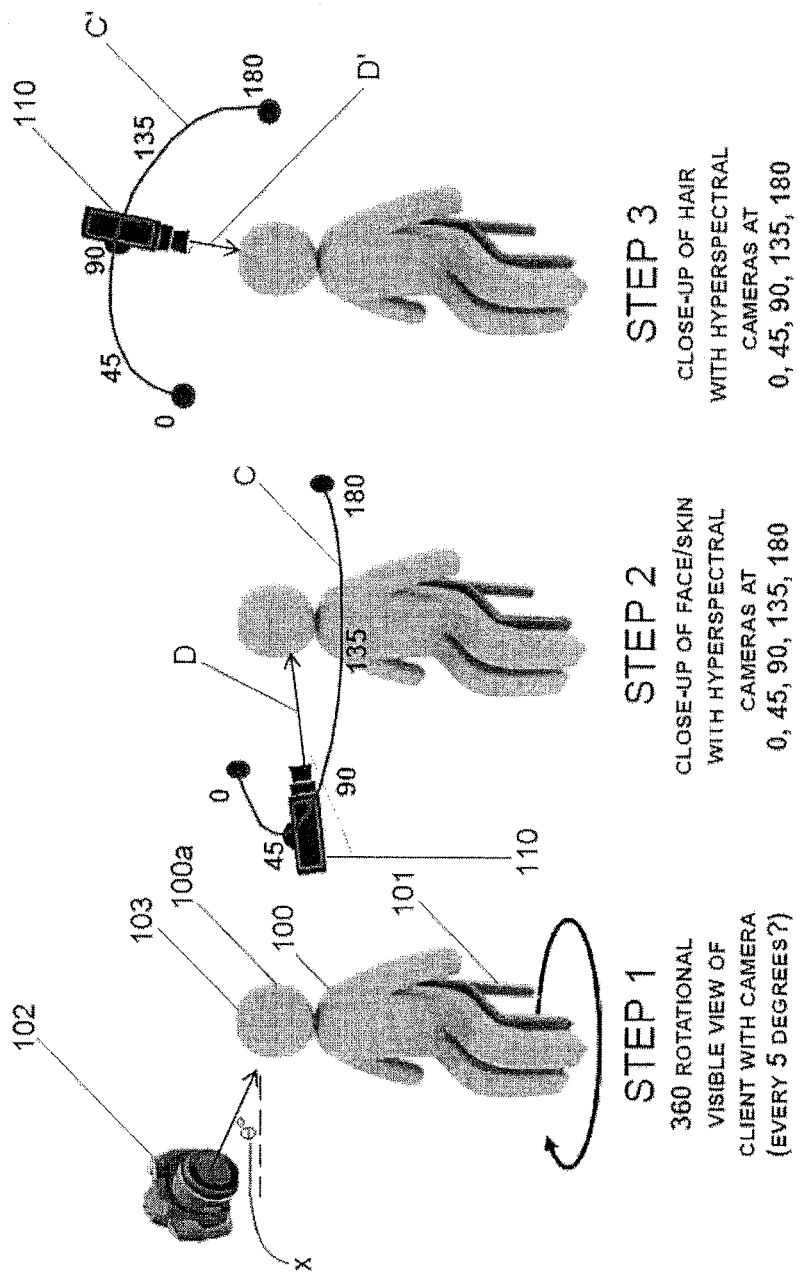

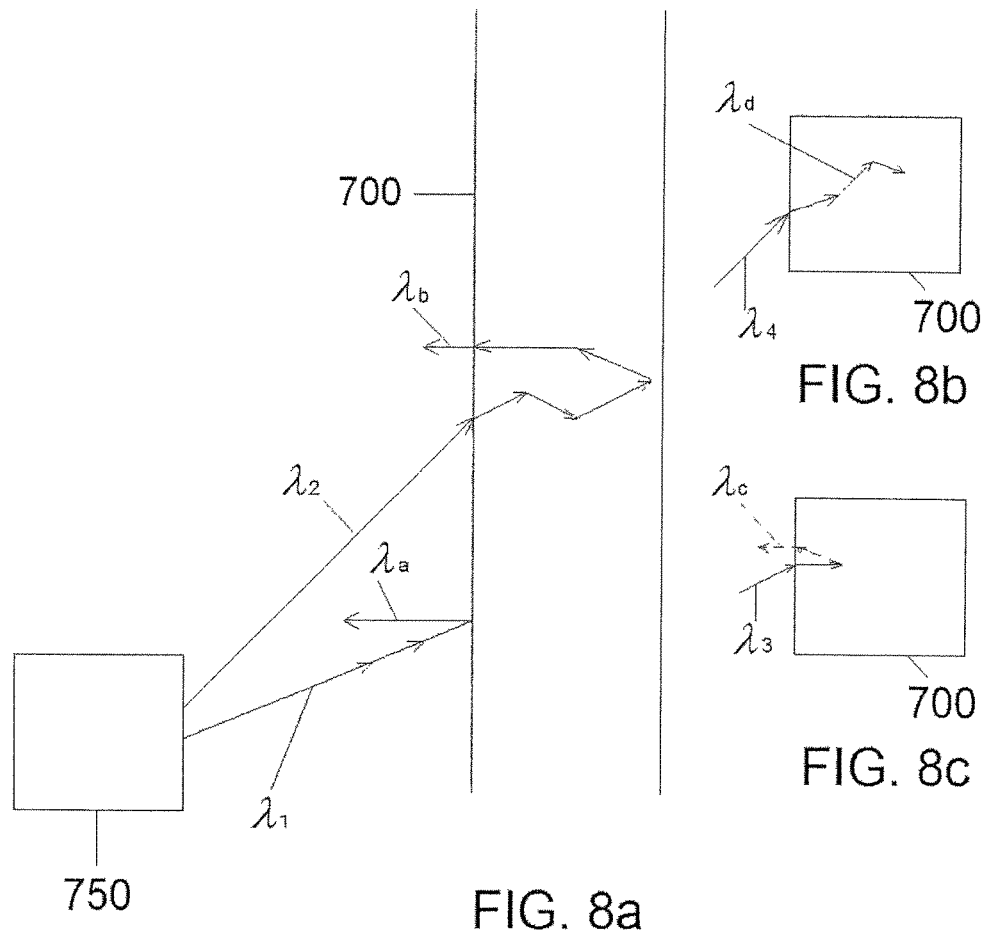

SYSTEM, METHOD AND DEVICE FOR ANALYSIS OF HAIR AND SKIN AND PROVIDING FORMULATED HAIR AND SKIN PRODUCTS

BACKGROUND OF THE INVENTION

1. Field of the Invention

The present invention relates to properties of hair and skin and their treatment, and more particularly for devices, methods and systems for evaluating skin and hair and for providing or generating a corresponding product application.

2. Brief Description of the Related Art

Beauty treatments often involve the use of products to enhance, repair or rejuvenate the skin, hair or body of an individual to improve or change the appearance or characteristic of the individual. One example of a beauty treatment involves hair coloring. Hair coloring compositions are used for coloring human hair. They may be applied by individuals in the home, or professionally in salons and studios. The purpose of hair coloring is to bring about a particular look with the color, which, for some individuals, may involve returning graying hair to its original color, and, for others, may involve altering the individual's hair color by changing it to a different color (which may be for reasons that the individual desires, such as, for example, a fashion, trend or style). Skin may be treated or enhanced with a number of compositions, including topical compositions as well as compositions that may be absorbed into the skin. Skin treatment compositions typically may include lotions, oils, creams, liquids, ointments, powders and the like. In some instances, skin may be treated with a colorant compound to provide a color to the skin. Cosmetics that tone the skin, hide blemishes, as well as compositions that change the effect or color of the skin (such as tanning colorants), also are used by individuals. The skin may react to certain conditions, such as aging, or exposure to elements, such as sun, wind, humidity or lack thereof. In some instances treatments may be applied to the skin to remediate an undesirable, unwanted or unhealthy condition. This applies to skin on the individual's body, both skin visible on the face, arms, legs, and other body portions, as well as the scalp which is typically covered by hair growth.

Skin typically is described as having three layers, the epidermis, dermis and a fat layer. The epidermis provides protection against foreign substances (e.g., bacteria, viruses) from entering the body, and also guards the internal structures of the body (e.g., organs, nerves, muscles, and the like). The epidermis may be thicker in certain areas of the body that typically require greater protection (e.g., the underside of one's foot). Keratin is one substance that is found in the epidermis. The outermost epidermis generally consists of dead cells, which are layers of these cells typically known as the stratum corneum. The next layer is the dermis which is a fibrous and elastic tissue. The dermis is generally composed of collagen, elastin, and fibrillin. Nerve endings, sweat glands and sebaceous glands (also known as oil glands), blood vessels, and hair follicles are found in the dermis. Below the dermis is the fat layer, which includes fat cells that are held together by fibrous tissue.

Hair is a substance of the body that is made up of a lipophilic cuticle layer, a hydrophilic cortex, and a medulla. Hair growth emerges from tubular like sacs in the scalp or skin which are called follicles and in which the hair root is contained. Hair is composed of a number of substances, such as proteins, including amino acids, and raw elements which are associated together with bonds to form the hair structure. Typically, human hair includes proteins, lipids, water, trace elements and pigments. The predominant component of a hair fiber is protein, which makes up about 91 percent of the hair fiber. A main hair protein is keratin. Hair that emerges from a follicle is generally a non-living fiber that is comprised of keratinized protein. Keratins are proteins, which, in addition to being a constituent of hair, are also found in skin and other mammalian tissues. Hair growth occurs by cells being produced in the follicle, at which point the cells have a nucleus and can absorb keratin, which is a fibrous protein. Once the hair cells grow, they extend from the scalp or skin, and the nucleus dies off. The color of an individual's hair is based on the pigmentation of hair follicles and involves two types of melanin, namely, eumelanin and pheomelanin. Eumelanin corresponds with darker hair, and typically, the greater the presence of eumelanin the darker the hair. Conversely, if less eumelanin is present, then the hair is lighter. The melanin levels of a person's hair may change over time. For example, a change in person's melanin levels may be visibly observed by the presence of gray hair. In addition, hair follicles of the same individual may have more than one color.

There are several major components of hair, which typically include several elements, namely, carbon (51%), oxygen (21%), nitrogen (17%), hydrogen (6%), and sulfur (5%). These elements bond together to form a number of amino acid proteins. Typical healthy human hair is considered to have the following representative amounts of amino acids:

Amino Acid Percentage in Healthy Human Hair Fiber
Cysteine 17.5%
Serine 11.7%
Glutamic Acid 11.1%
Threonine 6.9%
Glycine 6.5%
Leucine 6.1%
Valine 5.9%
Arginine 5.6%
Aspartic Acid 5.0%
Alanine 4.8%
Proline 3.6%
Isoleucine 2.7%
Tyrosine 1.9%
Phenylalanine 1.4%
Histidine 0.8%
Methionine 0.5%

As a result of the compositions that make up the hair fibers, the hair fiber often reacts to outside elements, such as the application of heat (which may be applied to curve or straighten the hair), or to compositions placed on the hair, such as dyes, shampoos, conditioners, bleaches, and the like. Hair fibers also may react to elevated temperatures, which can change the shape or structure of the hair fiber.

There have been attempts to ascertain the color of hair in order to provide a color match. There are some prior methods that utilize a visible color spectrum, or even UV and infrared, and may place a spectrophotometer on the hair to read a reflectance value. Some prior methods involve obtaining a color for hair by averaging the hair color over an entire field. But in such circumstances, averaging often leads to inaccurate readings, as, for example, hair that is brown with some white, may be read to be the same as light brown, which would take treatments differently, and provide different results for the same treatments.

However, variables associated with hair and skin, such as, their compositions as well as compounds that have been applied (e.g., purposeful treatments) or are otherwise present thereon as a result of exposures, or the production thereof by the individual's body, may affect the resultant hair or skin when it is subjected to a treatment. For example, where a hair has a treatment chemical on it, it may react differently when a further treatment is applied to the hair. In addition, human hair and skin may be varied in composition, and these variations also may affect the outcome or result of a treatment applied thereto. In many cases, an individual who desires to receive a skin or hair treatment typically selects the desired outcome, such as, for example, a color or tone for hair or skin, or a characteristic, for skin (or scalp) such as a moisturizer.

While a color match through a spectrophotometer reading may identify the particular color of an individual's hair or skin, since there are differences among the hair or skin of individuals, even though they may share the same hair or skin color, a treatment applied may have different effects for each individual. This means that the technician or other personnel must make an assessment of the hair or skin, and use observation and any experience to provide a solution. The determination is often subject to error and results typically vary based on the observation, correctness of judgment, background, training or lack thereof, and level of skill. Also, in many instances, a hair or skin condition or cause may not even be observable. In addition, another variable is that different salon personnel or technicians may from time to time handle different individual clients, or switch back, further leading to more variation. Furthermore, even where a salon personnel or technician is working with the same individual or client, any change from the standard would largely be experimental. In addition, individuals may change from time to time, due to factors such as age, health conditions, changes in diet, environmental exposures and other events. These changes typically may affect the operation of the treatment applied, and how it looks, as well as the suitability of the treatment. In some instances, only after the treatment is applied does it even become apparent that something has changed.

Some known drawbacks involved in some current salon services include the potential for improper processing of the hair, which may involve over-processing or under-processing. Typically over-processing of the hair may result in dry and damaged hair, which often is brittle and has the texture of straw. Over-processing may result from improper formulation of the color dye (which the salon typically mixes). Over-processing also may result from salon personnel failing to monitor the hair being treated. Combinations of improper formulations and lack of diligence in monitoring may provide undesirable results. However, where the formulation is off to begin with, even the most diligent monitoring may not remedy the situation. In many instances, starting with a formulation that is improperly mixed or constituted may constrain the efforts of the salon personnel, no matter how precisely they are following procedures. A salon technician typically is required to examine the hair of an individual before commencing a service. Hair characteristics need to be examined. Some observations may be made as to the overall condition of the hair, as well as individual considerations, such as, how dense the hair is (which generally is the number of hairs in a given unit area of the skin or scalp, such as per square inch), the hair texture (hair shaft diameter, whether thin or thick), and resistance (whether the hair is easily straightened or takes to chemicals). However, it is often difficult for salon personnel to identify the same characteristics in a uniform manner when inspecting an individual's hair. Different personnel may observe different properties, or consider one over another, or assign more importance to one. This may be based on background or simply how they go about providing a service. Due to variation between salon personnel, and the lack of consistency between salon personnel observations, even when examination of the hair is actually done, there is a potential for outcomes different than what was intended to occur. For example, hair and treatments on the hair may react to a newly applied chemical (such as a dye), and an adverse effect may result. Therefore, attempts to produce a target hair color may often result in something unintended, such as red or green tinted hair. Some chemical reactions may require correction, which takes further time. In other instances, the correction may need to be done days after the application of an improper chemical.

SUMMARY OF THE INVENTION

A method, system and device for determining the properties of hair and skin are provided. The method, system and device facilitates the selection of a proper treatment application to the hair or skin of an individual to achieve a desired target result. The hair properties measured may include the hair composition and chemical components of the hair, as well as coatings on the hair, and other substances on, absorbed or adsorbed on the hair. According to preferred embodiments, one or more hyper-spectral imaging components are employed to obtain information from the hair or skin.

According to some preferred embodiments, the imaging component may comprise one or more hyper-spectral cameras employed at a suitable distance from the individual's hair or skin to be measured. According to some preferred embodiments, hyper-spectral cameras are disposed at distances of about 2 to 5 feet from the individual's head, or skin.

According to some embodiments, the imaging components, such as hyper-spectral cameras, are configured to measure 2D arrays, as opposed to 1D or single "diodes". The hyper-spectral camera configuration views the entire hair as a spectral cube (preferably from the angle measured). The hyper-spectral imaging components, such as the hyper-spectral cameras, may view the person's entire face as a spectral cube.

Preferred embodiments of the invention are configured to measure across a wide range of wavelengths and preferably may include wavelengths from the visible to the thermal regions, such as, for example, from 400 nm to 12,000 nm wavelength). The method, system and device of the invention measure components of the hair. While components of the hair may provide particular colors to the hair (including reflectance of light of particular wavelengths, which we see as hair color), the present invention measures more than the visible color. Embodiments of the invention provide information that identifies the composition of chemicals comprising the hair, or constituting a coating or other substance on, attached to, or affecting the hair. Examples of some compositions that may be determined using the device, system and method, include chemicals that may be present in various hair colors, such as, for example, metal salt compounds, such as some common chemicals which affect hair and skin (i.e., caffeine).

According to preferred embodiments, the method, system and devices implement a hyper-spectral imaging component for determining actual or potential health conditions of an individual based on measurement of the hair, skin or near hair or skin surfaces. For example, the measurement or detection of certain compositions associated with the hair or skin of an individual, by being present as a component thereof, may be indicative of a particular health issue, or body activity. Hair color analysis typically compares colors, but there may be different components that are responsible for producing a color. The present invention is configured to provide a system, method and device that measures not only the color spectrum of the target, such as, for example, the hair or skin (treated or untreated), but the compositions of the target. Preferred embodiments determine the composition by conducting measurements with the device that preferably includes the 3000 nm to 12000 nm range (as well as the 400 nm to 3000 nm range).

The device, system and method may measure hair and skin in the same operation, so that once the imaging component, such as the one or more hyper-spectral cameras, records the information by imaging the head of an individual, both hair and skin conditions may be evaluated. The device, system and method preferably obtain information about the hair and skin. For example, in the same operation, both the hair spectrum and the person's facial skin spectrum may be obtained. The hyper-spectral information obtained may be used for coordinating, selecting and formulating hair and skin care products for the individual, and, in addition, may be used to detect the presence generally of chemicals which are in the person's body versus simply topical chemicals on the individual's hair or skin.

In connection with the hair products, the system, method and device provide information relating to potential products or chemicals that have been applied to the hair of an individual, as well as to the hair composition itself, underlying or on which the chemicals have been applied. The system, method and device measure the underlying composition of the hair or skin, so in the case, for example, of hair, the composition of the hair is computed from the hyper-spectral imaging information, which provides information as to how the hair will accept and react to different chemicals and treatments, such as, for example, bleaches, dyes, and the like. The information preferably may be coordinated with a hair or skin care product dispensing and formulating system, where recommended or custom formulated hair care products (e.g., shampoos, conditioners, coloring products, dyes) and skin care products (e.g., creams, lotions, powders) may be specified and provided for the individual. The system, method and device may implement the hyper-spectral camera imaging in conjunction with products for use at a salon, as well as personal care products that an individual may purchase or obtain based on the hyper-spectral information and analysis.

Embodiments of the device, system and method measure the surface as well as near surface conditions. For example, the surface of hair or skin may be measured to determine coatings and component composition or chemicals, and the near surface portions of the hair and skin, which may be below the surface level also may be measured and evaluated. The system, method and device may measure and evaluate surface or near surface conditions of an individual, such as the individual's hair and skin, and determine whether a health problem or other adverse condition is present. For example, a health problem that is present somewhere other than the locations being measured (e.g., other than the hair or skin) may be detected by the present system, method and device. The hyper-spectral imaging method obtains information and the devices and systems evaluate the hyper-spectral information to determine the presence of potentially adverse health conditions.

According to some preferred embodiments, the imaging components may be hyper-spectral cameras which may use a broadband light source which is provided either on-track or in-line with the camera. According to some alternate embodiments, the electromagnetic radiation that is directed at the individual subject may be provided from a tuned laser. Some embodiments may implement the measurement by utilizing the light source to shine a specific wavelength onto the subject target, such as the individual's hair or skin, as that same wavelength is being measured by the hyper-spectral camera. According to some embodiments, there is a synchronized stimulus to the hair from a low power laser that is swept in wavelength. The response of the subject hair or skin to the wavelength energy is recorded using the hyper-spectral camera detectors, so that for each wavelength or wavelength band a response is recorded that also identifies the spatial location.

The device, system and method also include a calibration mechanism for calibrating the components to facilitate consistency among measurements and among different individuals. According to some embodiments, a calibration element, such as, for example, a swatch, may be placed on the individual's hair or skin. The calibration element provides a known precise spectral response in order to insure that measurements are continuously calibrated irrespective of instrumentation ageing or other measurement conditions, and/or ambient light.

According to preferred embodiments, the imaging components may be controlled with a processor and software configured with instructions for implementing capture and storage of the subject response to the electromagnetic energy, which may be determining reflected electromagnetic energy, absorbed energy, scattered energy, transmitted energy, or other light energy effect detected from the individual's hair and skin, as well as the relative location of the hyper-spectral imaging component and individual (such as the location from which the response recorded by the detector same). Further software for generating a map from the hyper-spectral imaging information may be provided on or in association with the hyper-spectral imaging camera or, alternatively, on a remote computing unit that is configured to receive the hyper-spectral imaging information (in processed or unprocessed form). Responses from the calibration element may be used to adjust the recorded data of the detectors for the hair and skin responses to electromagnetic wavelength energy. According to embodiments, the reflection may be measured as the fraction of light reflected from a surface as a function of wavelength. According to preferred embodiments, reflected light is measured. According to some alternate embodiments, transmittance or scattering may be measured.

According to preferred embodiments, the hyper-spectral imaging system includes components which may be used for conducting the evaluation of the skin and hair. The components may be linked with or otherwise associated with product dispensing equipment.

According to some embodiments, a hair or skin map is provided. The hair or skin map preferably is generated from the hyper-spectral imaging information, and maps the target being measured, such as the individual's hair and skin. The map provides information across the individual's entire hair or skin, and therefore, is able to take into consideration differences in the colors, including, for example, different dyes, bleaches and colorants that may be applied to different areas of the hair. For example, the map preferably distinguishes between areas of the hair where there are highlights, color streaks or which are base colors.

A plurality of areas of the hair or skin are selected and the spectral imaging information is processed to automatically ascertain treatments necessary to restore the skin, hair or scalp to a desired condition, or alleviate an undesirable condition. In the case of hair, the desired condition may be the hair color, or may be another hair characteristic, such as, for example, a hair property, (e.g., remediation of a dry or damaged hair condition).

In some embodiments, the processing system is configured to select several areas of skin, scalp and hair to produce detailed spectra and automatically ascertain the treatments necessary to restore skin, hair or scalp to a desired status condition or color. In other words, color, as well as other characteristics of the hair or skin health may be addressed and manipulated by implementing the present system.

According to some preferred embodiments, the hair map, skin map, or hair and skin map is constructed to provide information across the hair or skin, and preferably provides detailed characterization of the entire body of hair or face or skin, and not from just in one place on the hair or skin.

Embodiments of the invention provide an input device for obtaining data about a condition of an individual, and more particularly, of an individual that is to receive a cosmetic treatment from a dispensing device. The treatment preferably is a target treatment that is provided or customized for the individual. Embodiments of the invention preferably link the input device with a dispensing device, such as, for example, the dispensing apparatus of Colorculture Network, LLC's U.S. Pat. No. 8,977,389, the complete disclosure of which is hereby incorporated by reference. According to some preferred embodiments, the condition of an individual is a condition associated with a keratinous substance, such as, for example, the individual's hair, skin, nails and the like. According to an exemplary embodiment, the condition for which data is obtained is that of an individual's hair, and the treatment is a hair treatment composition, such as, for example, a shampoo, conditioner, strengthener or colorant. The input device, according to a preferred embodiment, is used to obtain information about the individual's hair. Preferred embodiments ascertain hyper-spectral data of an individual's hair (or skin) which is analyzed to determine the individual's hair properties (or skin properties). Properties may include, for example, substances, treatments, components of the hair (or skin), which may affect the reception or effect of a hair (or skin) application. According to preferred embodiments, the input device is configured to encompass a broad spectral range, and may include the visible spectrum or portions thereof, and infrared regions as well.

The hyper-spectral imaging components and system may be utilized to generate formulas for hair and skin using the information obtained from the analysis and evaluation of the hyper-spectral information or data. For example, the present devices, systems and methods shown and discussed herein, may be associated with or incorporate the dispensing apparatus of U.S. Pat. No. 8,977,389 or one or more features or components thereof. The complete disclosure of U.S. Pat. No. 8,977,389 is herein incorporated by reference.

BRIEF DESCRIPTION OF THE DRAWING FIGURES

FIG. 1 is a schematic illustration showing an individual and an imaging environment, where a first camera is provided to image the individual, which may include imaging of the individual's hair, skin or both.

FIG. 2 is a schematic illustration showing the individual in an imaging environment, where a hyper-spectral imaging component is depicted.

FIG. 3 is a schematic illustration showing the individual in an imaging environment, where a hyper-spectral imaging component is depicted imaging from different positions.

FIG. 7b is a planar section taken from the datacube of FIG. 7a.

FIG. 7c is a plot of a location spectrum depicting reflectance versus wavelength for a particular spatial coordinate or pixel $X_A, Y_B$ along the x-y axis of the datacube represented in FIG. 7a.

FIG. 8a is a diagram illustrating a portion of a hair follicle with potential actions of the electromagnetic radiation.

FIG. 8b is a diagram illustrating a portion of a hair follicle with potential actions of the electromagnetic radiation.

FIG. 8c is a diagram illustrating a portion of a hair follicle with potential actions of the electromagnetic radiation.

DETAILED DESCRIPTION OF THE INVENTION

Figure 4:
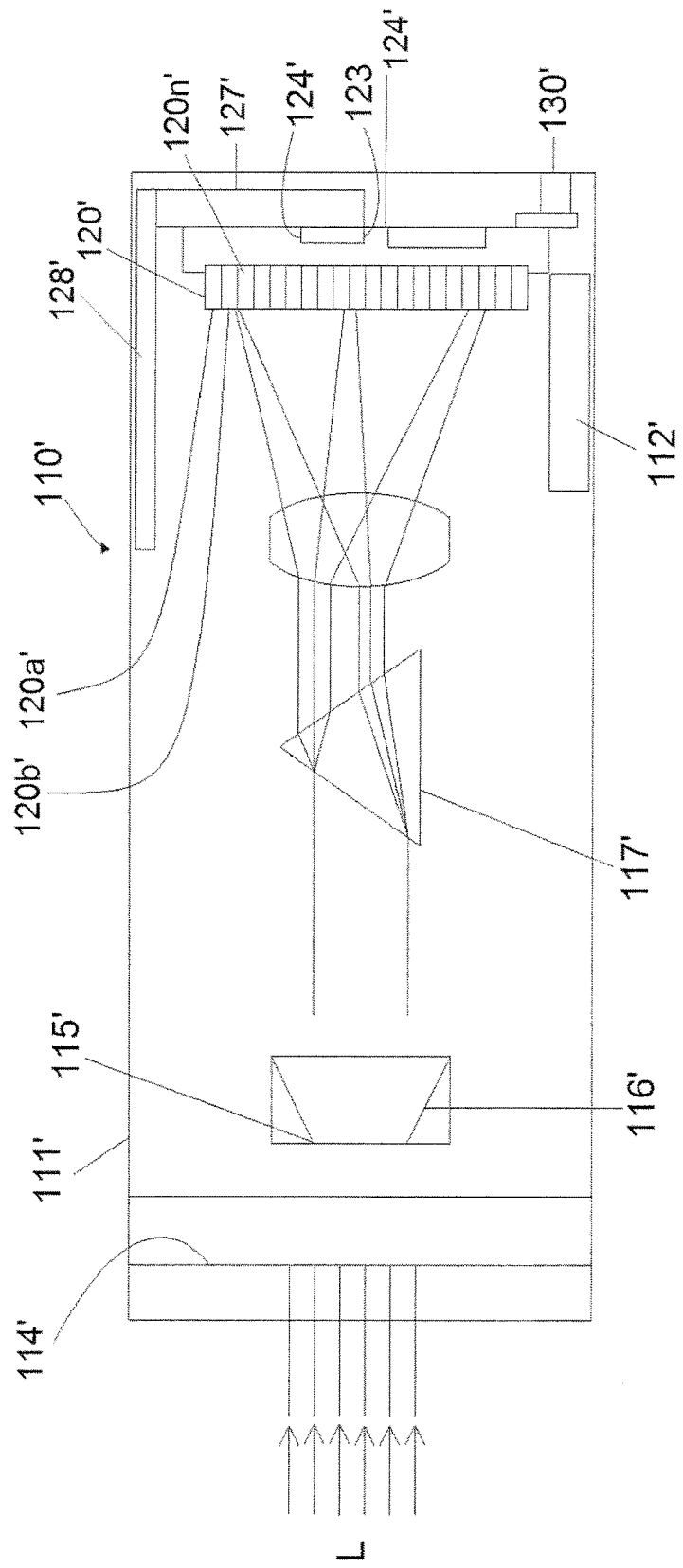
FIG. 4 is a schematic illustration of an exemplary embodiment of a hyper-spectral imaging component.

Referring to FIGS. 1 to 3, a preferred embodiment of a method, device and system for measuring hair and skin properties is shown. An individual 100 is depicted for reference seated in a chair 101. A first capture component comprising a camera 102 is shown in FIG. 1 for capturing the individual's target body portion, which, in this example, is the individual's head 100a, which includes the hair 103 and skin 104. According to a preferred embodiment, the camera 102 captures a plurality of images of the individual from different positions. The first camera may be a digital camera capable of recording and storing an image of the individual's hair 103 and skin 104. According to a preferred embodiment, the camera 102 captures a rotational view encircling the individual 100, and more particularly the target area, the individual's head 100a. The camera images the individual's head 100a in a visible view, which includes the visible spectrum wavelengths. According to one exemplary embodiment, the camera 102 may be configured to image at circumferential intervals about the target. According to some embodiments, a plurality or bank of cameras 102 may be provided and arranged about the location of the individual to record images from a respective plurality of different directions. For example, according to some embodiments, at least one or the other of the camera 102 and individual's head 100a moves relative to the other, so imaging of the individual 100 may take place from a plurality of locations using a single camera 102 or a number of cameras 102, which may be less in number than the number of image locations about the individual from which images are to be taken. According to some embodiments, for example, the camera 102 may be configured to obtain images every 5 degrees, so that there are about 72 images taken about the person's head 100a. The plurality of images may be mended together using any suitable technique to provide the image of the individual 100. For example, the images may be processed to generate a display of an effective three dimensional rotatable view of the individual, which may be manipulated on a display screen to display different perspectives and angles. The camera 102 may be handheld, or more preferably, is carried on a mount or structure. For example, a mounting structure may be provided to hold the camera 102, and to move the camera 102 about the individual 100. According to one embodiment, the camera 102 is mounted for movement circumferentially about the individual's head 100a. Preferably, the camera 102 images the individual's head 100a from an angle x degrees, slightly above the individual's face. The camera 102 may be rotated to make one or more revolutions about the individual 100. An image capture of the individual 100 is therefore stored. According to some other embodiments, a plurality of cameras 102 are provided, and may be fixed in position relative to the individual 100, or depending on the number of cameras 102, may be arranged about the individual 100, such as, for example, circumferentially, on a structure to rotate relative to the individual 100 and capture images from a plurality of different locations.

Referring to FIGS. 2 and 3, an imaging component, shown configured as a hyper-spectral capture component, represented as hyper-spectral camera 110, is provided to capture information about the individual's hair 103 and skin 104. The hyper-spectral camera 110 is shown, and according to some preferred embodiments, a plurality of hyperspectral imaging cameras 110 may be employed. As shown in FIG. 2, the hyperspectral camera 110 (or cameras) preferably is arranged a distance D relative to the individual to be close up thereto. FIG. 2 shows an example where the hyper-spectral camera 110 is arranged to image the individual's head 100a, and more particularly the individuals' skin 104. According to some preferred embodiments, the hyper-spectral imaging cameras are arranged a distance of about 2 to 5 feet from the individual 100, and preferably the distance is uniform from the points of imaging. In FIG. 2, a single hyperspectral camera 110 is shown disposed at a relative axial location of 45 degrees. The hyperspectral camera 110 may be configured for movement relative to the individual 100 similar to that discussed above in relation to the camera 102 so that the hyper-spectral camera 110 may be positioned at a plurality of locations), or, according to some preferred embodiments, a plurality of hyper-spectral cameras 110 may be provided and arranged about the individual 100. For example, the hyperspectral cameras 110 may be provided at locations around the individual 100. According to one preferred embodiment, hyper-spectral imaging of the individual's head 100a, including the hair 103 and skin 104, is carried out by obtaining a plurality of hyper-spectral scans or images at a plurality of locations. A preferred arrangement, according to an exemplary embodiment, is illustrated in FIG. 2, wherein hyper-spectral images are taken of the individual at 0, 45, 90, 135 and 180 degrees about a circumference C.

Referring to FIG. 2, hyper-spectral cameras 110, may be provided at each axial imaging point, such as, at 0, 45, 90, 135 and 180 degrees about the circumference C. The hyper-spectral imaging cameras 110 preferably may be operated synchronously, but according to other embodiments or arrangements may be operated asynchronously.

Figure 6:
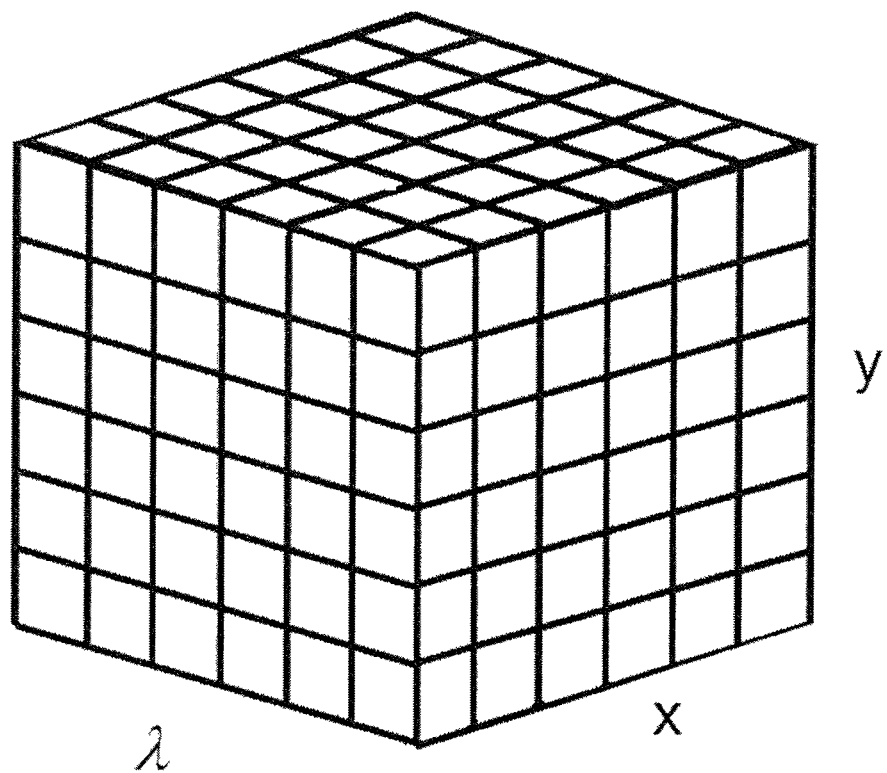
FIG. 6 is an illustration of a representation of a datacube obtained from a hyper-spectral imaging information.

According to preferred embodiments, the hyper-spectral imaging camera 110 preferably is configured with a 2D detector array. The implementation of the 2D detector array enables the data to be obtained for the image, which according to preferred embodiments, may comprise a collection of a vertical slice of the datacube at once. According to the 2D detector array implementations, only one spatial dimension needs to be scanned to fill out the cube. An exemplary depiction of a hyper-spectral datacube is shown in FIG. 6. Although the blocks are shown as a convention to represent responses to wavelengths for a location or pixel, the cube, an actual image obtained may include areas of greater and lesser response (typically brighter or more intense or darker and washed out). The datacube represents the information collected utilizing the hyper-spectral imaging component, such as the camera 110.

Referring to FIG. 3, a hyper-spectral camera 110 is shown arranged at a distance D' (which may be the same or different than the distance D shown in FIG. 2). A preferred distance from the individual's hair 103 may be about 2 to 5 feet. According to preferred embodiments, a plurality of hyper-spectral cameras 110 may be employed to image the individual's hair 103. According to a preferred embodiment, the hyper-spectral cameras are arranged to image close-ups of the individual's hair 103. The hyper-spectral camera 110, or cameras, preferably are arranged to image the hair from a plurality of locations or positions. For example, as shown in FIG. 3, in accordance with a preferred embodiment, the hyper-spectral cameras 110 are provided to image the hair and may be provided at each radial imaging point, such as, at 0, 45, 90, 135 and 180 degrees about the circumference C'. The hyper-spectral cameras 110 may be disposed above the hair 103, so that the capture takes place from and between points on each side of the individual's head 100a, such as those points 0 degrees and 180 degrees (shown in FIG. 3), and a plurality of points therebetween, such as, for example, the points at 45, 90 and 135 degrees. The hyper-spectral camera 110 shown in FIG. 3 may be arranged as a bank of cameras, or one or more cameras provided on a frame for movement across the circumferential path C', or any other arrangement, including the arrangements discussed herein in connection with the skin imaging shown in FIG. 2. For example, in accordance with the illustration in FIG. 3, according to a preferred embodiment, hyper-spectral cameras 110 preferably may be arranged radially perpendicular to the imaging direction shown.

The hyper-spectral imaging cameras 110 preferably are employed in conjunction with spectral processing components, which may be configured as part of the camera 110, or separately provided to receive and process information from the camera 110. The imaging system preferably includes a radiation source. For example, in connection with image recording in the visible spectrum, one or more lights may be used, and may be provided near or directed at the individual 100 being imaged. The light source preferably includes a bulb or other means for generating or emitting radiation of wavelengths in the visible spectrum range. According to preferred embodiments, the spectral range for the visible imaging is preferably between about 400 nm and 700 nm, and may be expanded to 1500 nm to cover infrared. A radiation source for emitting electromagnetic radiation in the wavelengths of about 3000 nm to about 12,000 nm is provided in conjunction with the hyper-spectral cameras 110. Wavelengths of electromagnetic radiation preferably encompass a range of about 400 nm to about 12000 nm. A source of electromagnetic radiation is provided, and may include a generator, one or more filters, or a tuning mechanism to provide emission of electromagnetic radiation of discrete wavelengths, which may be provided in spectral bands, or separately, over the spectral region being evaluated.

According to some preferred embodiments, the hyperspectral camera 110 may be provided with a radiation generating source, such as, for example, a pulse laser, so that emissions of wavelengths of interest that are being measured may be directed to the target, such as, the individual's skin or hair. According to some preferred embodiments, the electromagnetic radiation source comprises a broadband light source. The light source may be provided to illuminate the subject so that reflected light from the subject may be detected by the imaging component. For example, the light source may be provided on-track or in-line with the hyperspectral imaging component or camera. An alternate embodiment includes a tuned laser, configured to shine a specific wavelength onto the hair or skin as the same wavelength that is being measured by the hyper-spectral imaging component or camera. Preferably, there is a synchronized stimulus to the hair or skin (in its entirety or the location being measured) from a low power laser that is swept in wavelength. According to preferred embodiments, the imaging component is configured to synchronize its detection at specific wavelengths (or wavelength bands) with the wavelength being emanated by the laser (or other illumination source). The spectral wavelengths preferably are measured from the visible through the thermal (e.g., 400 to 12000 nm). Alternatively, the radiation source may be provided on or separate from the hyperspectral camera. Examples of reflected radiation are depicted in FIG. 8a in connection with a hair sample 700. A light source 750 is represented in the diagram, and may be any suitable light source for providing the electromagnetic radiation at the wavelengths required for imaging (including, for example, as discussed herein). The hair sample 700 is shown as a single hair for illustration, and preferably, embodiments image a plurality of hairs, typically the hair on the individual's head. Electromagnetic radiation $\lambda_1$ (of wavelength 1 or wavelength band 1) is directed at the hair sample 700. The hair sample 700 shows $\lambda_a$ which is reflected electromagnetic energy. The hair or coating on the hair, such as, for example, a hair dye, reflects the electromagnetic radiation ($\lambda_a$). Electromagnetic radiation $\lambda_2$ (of wavelength 2 or wavelength band 2) is directed at the hair sample 700. The electromagnetic radiation $\lambda_b$ illustrated to represent scattering of the radiation. According to this example, the scattering may take place on the surface, and, also may take place within the structure of the hair 700 (see, e.g., FIG. 8c, electromagnetic radiation $\lambda_3$ (of wavelength 3 or wavelength band 3) is directed at the hair sample 700 and see the scattering of wavelength $\lambda_c$). In FIG. 8b, electromagnetic radiation $\lambda_4$ (wavelength 4 or wavelength band 4) is directed at the hair sample 700 and wavelength $\lambda_d$ is shown being absorbed by the hair 700, which may be absorbed by one or more components within or making up the hair 700. Other potential actions of the electromagnetic radiation encounters with the hair 700 are possible, and may include scattering and then an emission of light that is shifted. In some instances, absorption may be followed by luminescence (where the molecules or substances making up the hair react to the electromagnetic radiation energy wavelength encountered).

In connection with the operations, the individual may be provided with coverings, such as, for example, sun glasses or other shielding products. Alternatively, the system may be implemented to process the information and provide the individual with a visible display, so the individual may view the imaging, representations of the imaging, or information based on the processed image information.

In the configuration illustrated in FIGS. 1 to 3, the electromagnetic radiation (e.g., such as a lighting source) preferably may be provided to illuminate the subject, or portion of the subject, such as the hair or skin. According to some embodiments, the radiation source or lighting (not shown) may be in the same axis as the center focus of the imaging camera, or, according to some other embodiments, may be at an angle to it (for example, to obtain polarization data). Alternatively, the system, method and devices may be utilized by providing a general illumination of the subject with lighting from a light source or a plurality of light sources. The electromagnetic radiation preferably is provided to emit at the wavelength spectrum being evaluated, or the radiation may be manipulated such as with a filter, to deliver the desired wavelength radiation to the subject.

The information obtained through imaging the hair and skin in the visible wavelength spectrum provides details about the color and visible condition of the individual's skin and hair. However, the visible color may be due to components making up the hair, or may be the result of chemicals applied to the hair, such as, for example, bleaches, dyes and other compounds. In a first imaging step, the first camera 102 preferably obtains information from visible spectrum imaging, and the information may be processed to determine visible spectral values of the individual's skin 104 and hair 103 and produce a digital image for reproduction and displaying. However, the hair color may be indicative of naturally colored hair as well as treated hair, such as hair that is dyed, bleached or otherwise altered. Further steps involve one or more second imaging steps which involve obtaining hyper-spectral information for the target hair or skin.

The hyper-spectral camera or cameras 110 provide information about the spectral condition of the target, such as, for example, the individual's skin 104 and hair 103. Hyper-spectral information obtained for an individual may be processed to determine hair and skin characteristics and properties.

According to a preferred embodiment, the hyper-spectral imaging component may be constructed having an optical dispersing element that splits the incoming light into its many narrow, adjacent wavelength bands. The incoming light preferably may be light that is reflected light from a source, or reflected from a mirror (which may receive a direction of light from a source). According to preferred embodiments, the reflected light that is measured is light that is reflected from the hair or skin of a person. The light may be provided from a light source, such as, for example, a directed light source, diffuse light source, or other suitable method or devices for providing light onto the hair or skin. The target receives light or is in an environment where light is present. In the case of the hair or skin, the light is reflected. The hyper-spectral imaging component preferably includes a plurality of detection elements. The detection elements may be configured to detect specific wavelengths of light or light energy (e.g., electromagnetic radiation). According to preferred embodiments, the hyper-spectral imaging component is configured with banks of detectors. In one arrangement, each detector is configured to measure a separate wavelength, or a span of wavelengths (typically refined to as a wavelength band). In another arrangement, the detectors measure a range of wavelengths, and the wavelength of interest is radiated at the subject and the detector measures the response. Some preferred embodiments of the hyperspectral imaging component include separate detector elements for each respective band. The bands may be separated by groups of adjacent wavelengths, such as, for example, every 10 nm, every 20 nm, or other suitable band. The hyper-spectral imaging component measures spectral energy in discrete bands. The detectors preferably receive light reflected from the target subject hair or skin. The reflected light may be direct or indirect, meaning its path may be manipulated with one or more components, such as, for example, lenses, mirrors, reflective foils and surfaces, and the like. According to preferred embodiments, the hyper-spectral imaging component includes a dispersing element which breaks down the reflected light into many narrow bandwidth ranges or bands. The light therefore is separated into its individual energy components, or groupings thereof, such as bands of energy. The bands represent a range of wavelengths, and more preferably, bands of adjacent wavelengths.

One preferred example of a dispersing element is a grating or prism onto which the reflected light is directed or focused. The component light from the dispersing element is directed to the plurality of detectors. Preferably, the detectors are arranged to correspond with the grating or prism, so the light dispersion is directed onto a detection element suitable to detect the presence or absence of the energy band, or wavelengths in the band. According to some alternate embodiments, a tunable laser or other filters are provided to produce a discrete wavelength radiation (or wavelength bands), and the detection is synchronized to detect the response to the discrete wavelength or band. The plurality of detectors of the hyper-spectral imaging component may be configured to detect and record spectral measurements of bands as narrow as 10 nm, micrometers, or wider range bands. The band range, 10 nm or other band range number (larger or smaller), may be made through a wide range of the spectral range, such as, for example, according to preferred embodiments, from about UV, visible, infrared, and beyond. According to some preferred embodiments, the hyper-spectral imaging component is configured to detect energy that includes wavelengths from the visible to the thermal regions, such as, for example, from 400 nm to 12,000 nm. The bands may be in 10 nm bands, or other suitable band range (i.e., greater or smaller). Preferably, the bands are adjacent bands. According to some embodiments, the bands may be equal in their ranges, e.g., a plurality of 10 nm bands over the spectral range (e.g., from 400 nm to 12,000 nm), or alternatively, according to some other embodiments, the bands may be grouped, in narrow bands for certain of the range or ranges, and wider bands for other of the ranges. According to some alternate embodiments, the hyper-spectral imaging may take place with wavelength bands that include one or more consecutive or adjacent bands (or groupings of bands) with skips between the adjacent bands (or groupings). For example, according to some alternate embodiments, a first hyper-spectral range and second hyper-spectral range may be utilized for imaging. According to one exemplary alternate embodiment, a first hyperspectral range may be from about 400 nm to about 700 nm and a second hyperspectral range may be from about 900 nm to about 12000 nm, (skipping 700 to 900 nm).

According to some embodiments, the first camera may image over the visible wavelengths of light, e.g., 400 to 700 nm. Alternatively, the hyper-spectral imaging component also may image the spectral range that encompasses the visible camera range, but is obtained with the hyper-spectral imaging component and detectors provided therein. The hyper-spectral imaging data provides further and unique information (even for the same visible range images that the first camera may detect) that the imaging obtained with the first camera 102.

The hyper-spectral imaging component preferably may be configured to comprise a hyper-spectral camera having optical components that direct and/or focus the reflected light from the target subject, and more preferably, light reflected from the hair and skin of the target subject, onto the grating or diffusing component, and to the plurality of detectors. The detectors provide a signal response based on the reflected light and its constituent wavelengths. The hyper-spectral information or data is stored and processed to provide information about the target individual's hair and/or skin. Referring to FIG. 4, a schematic illustration of a hyper-spectral imaging component 110' is shown configured as a hyper-spectral imaging camera. The hyper-spectral imaging component 110' according to a preferred embodiment, has a housing 111' for housing the components. The housing may carry one or more components therein and protect them or may support them on the housing 111'. A power supply 112', such as, for example, a rechargeable battery, may be provided to power the hyper-spectral imaging component 110'. Alternatively, the power may be supplied to the component 110' by an external source, such as, a wall outlet or other source. The housing 111' preferably includes a front panel 113' with an opening 114' therein. The electromagnetic radiation that is reflected from an object, such as, for example, the target subject (see e.g., FIGS. 2 and 3), may enter the component 110' by passing through the opening 114'. The reflected light L may be directed by a directing component, such as an optical component, within the housing 111'. For example, reflectors, such as mirrors 115', 116', may be used to direct the light L. In the exemplary embodiment illustrated, the light L reaches a diffusing component, shown as the grating or prism 117'. The grating or prism 117' separates the light into its component wavelengths. The prism 117' and light shown in FIG. 4 is for illustration purposes, and the grating or prism 117' may refract light at angles different than what is shown in the illustration. Preferably, the grating, such as a prism, breaks down the light into its component wavelengths, which may be detected and measured by the detector cells 120a', 120b' . . . of the sensor 120' and associated circuitry 124'. According to some alternate embodiments, band pass filters (which are fixed or tunable) may be provided to move in and out of the scanning light path. According to some embodiments, the band pass filter may be utilized for particular detection or particular wavelengths (for example, to determine the presence of absence of a particular wavelength exhibiting substance, e.g., bleaching compound). One or more optical elements, such as for example, the lens 118', may be provided to direct the component light onto particular detectors of the sensor 120'. The sensor 120' may be comprised of a number of individual detector cells (see e.g., 120a', 120b', 120n', 120n+1') for detecting a wavelength of a particular energy. A processing component, such as a computer hardware processor 123' may be provided and preferably is configured in a circuit 124' with other electrical components of the device 110'. For example, according to some embodiments, the processing component is provided as part of a microcontroller, with software configured to process the readings from the detector sensor 120' and cells 120a', . . . . According to some embodiments, the detector cell 120a', 120b', . . . is configured to represent pixels on an image area designated by the x,y axes. The wavelength, λ, may be represented by an additional axis (e.g., see FIGS. 6 and 7a). The device 110' also may include communications components for transmitting the information or signals, either processed or unprocessed from the sensor, microcontroller or other device circuitry to a remote computing device, such as, for example, a server or other computer. The hyper-spectral imaging component, although illustrated having an opening 114' and mirrors 115', 116', may be configured with alternate arrangements of mirrors, lenses and reflectors. For example, the reflectors or mirrors may be provided to direct the electromagnetic radiation or separated wavelength light or energy onto the detector 120'.

According to some preferred embodiments, the hyper-spectral imaging component 110' is configured to communicate with a dispensing apparatus that dispenses a product that may be used by the user. For example, the imaging component 110' may be configured to communicate information to a remote computer device, such as a server, that controls the dispensing apparatus to generate a beauty product, such as a hair or skincare product. The product may be generated based on a desired target or effect that the target individual desires to achieve. The information from the hyper-spectral component is processed and used to implement a formulation or changes to an existing formulation to provide a product for the imaged hair or skin. The imaging component 110' may be linked to communicate information directly to a dispensing apparatus, an evaluation apparatus, or a remote component that controls the dispensing apparatus or evaluation apparatus. Embodiments of the invention preferably link the input device with a dispensing device, such as, for example, the dispensing apparatus of Colorculture Network, LLC's U.S. Pat. No. 8,977,389, the complete disclosure of which is hereby incorporated by reference.

According to a preferred embodiment, the hyper-spectral imaging component 110' may include a transceiver 127' and an antenna 128'. The imaging component 110' preferably includes one or more ports 130' for connecting with a cable (not shown) in order to transmit information from the imaging component 110' and any sensors or circuitry therein through a hard wired connection (or port connector/transmitter). Alternatively, or in addition, the imaging component 110' may include wireless networking communications components configured to connect through a wireless network (e.g., Wi-Fi and the like).

Figure 5:
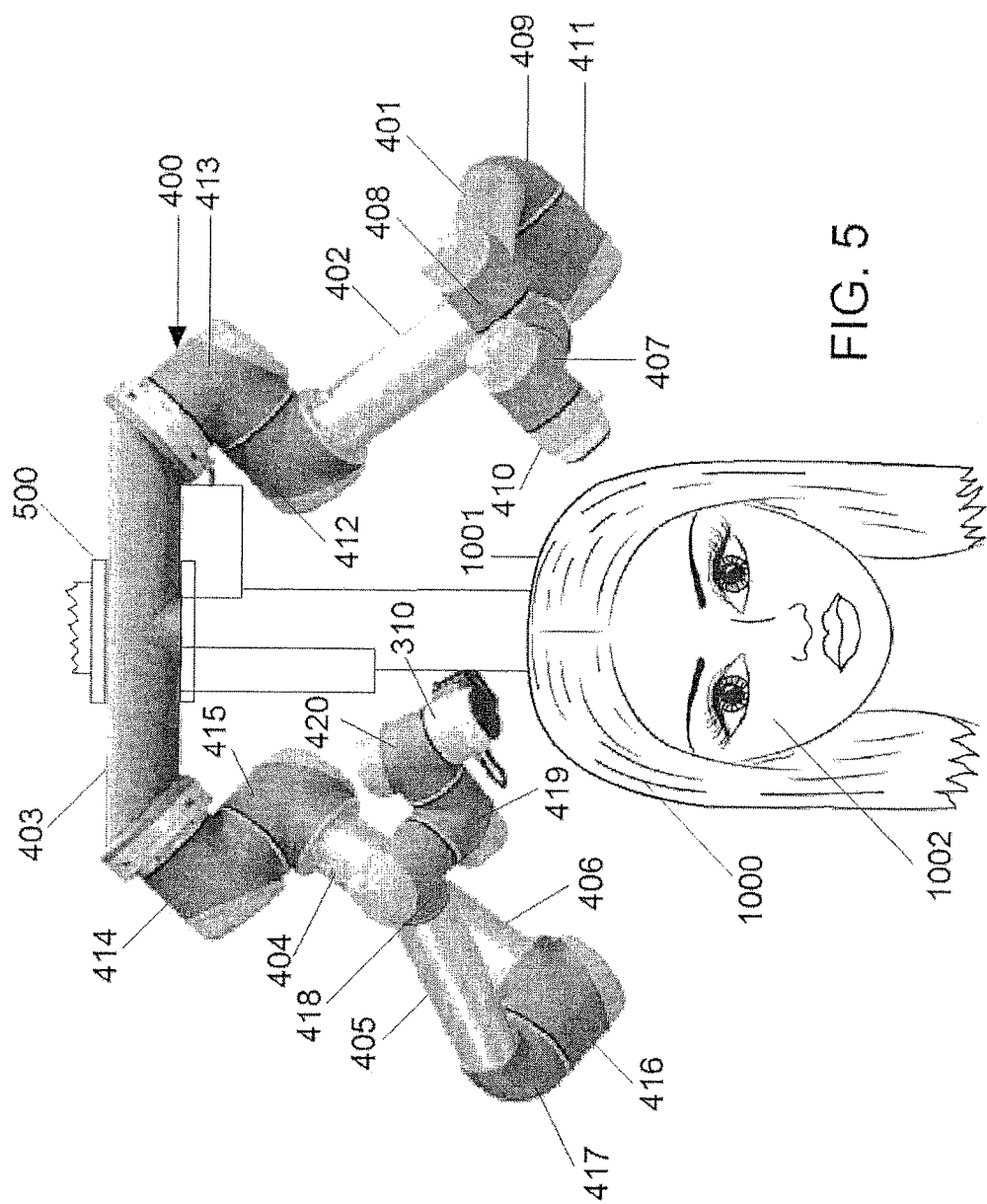
FIG. 5 is an illustration of an exemplary embodiment of a mounting arrangement for supporting one or more hyper-spectral imaging components.

Referring to FIG. 5, other exemplary embodiments of hyper-spectral imaging components 310,410 are illustrated supported on a frame 400. The frame 400 is shown in an exemplary embodiment with a plurality of frame sections 401,402,403,404,405,406, and a plurality of joints 407,408, 409,411,412,413,414,415,416,417,418,419,420. A mounting support 500 is shown for holding the frame 400. The mounting support 500 may be movable to provide the frame 400 and imaging components 310,410 carried thereon to be adjusted or positioned to accommodate an individual's height or size, or to position the location of the cameras 310,410. A plurality of connecting members, such as, for example, the connecting joints 407,408,409,411,412,413, 414,415,416,417,418,419,420, may be utilized to provide further movement of the imaging components or cameras 310,410. The hyper-spectral imaging cameras 310,410, may be operated separately, simultaneously or serially, while the frame 400 is in motion so that the individual 1000 may be imaged by having the cameras 310,410 move about the hair 1001 and face 1002. The joints 407,408,409,411,412,413, 414,415,416,417,418,419,420 may be movably connected. According to some embodiments, a moving mechanism is provided to motorize the joint connections for movement. Movement of the joints 407,408,409,411,412,413,414,415, 416,417,418,419,420 may be controlled to position the cameras 310,410 at appropriate locations relative to the individual 1000 for imaging. According to some embodiments, the frame 400 may be configured to be moved away from the individual once imaging has concluded, so that the individual will not accidentally contact the cameras 310,410. The depiction in FIG. 5 represents one embodiment, and the imaging components, such as, one or more cameras, may be utilized to obtain information from an individual using configurations other than those shown in FIG. 5. The hyper-spectral imaging camera 310,410 and frame 400 may be utilized in connection with or in place of the hyper-spectral imaging system shown in FIGS. 1-3.

The hyper-spectral imaging component preferably is configured with communications elements, such as, for example, wired or wireless, radio, Wi-Fi, Bluetooth, or other components and circuitry to communicate captured information from the detectors. The hyper-spectral imaging component or camera may include circuitry that is provided to process and store, and/or communicate the information from the detectors, and other components of the hyper-spectral imaging component or camera to a remote location. The remote location may be a network node or communication component, and, preferably may be or ultimately may be a server or other device that includes a processing component and storage media with software containing instructions for implementing the evaluation and analysis of the hyper-spectral information, and, preferably, may evaluate and analyze the visible camera image information.

The invention also preferably provides spectral libraries or databases, in which hair and skin component spectra information may be stored. Hair is composed of a number of substances. These substances may be different from individual to individual depending on diet, environmental exposures, pharmaceutical and medical conditions and treatments, as well as hair and other topical treatments, such as, dyes, bleaches, shampoos, conditioners, strengthened and the like. The difference may be in the presence or absence of a substance or its abundance of scarcity. The hyper-spectral imaging information is processed to provide further evaluation of the hair and skin as well as particular constituents that may be included in the hair and skin. Exemplary embodiments of hyper-spectral imaging processing are depicted in the diagrams illustrated in FIGS. 9 and 10. In some instances, compositions that form or are included in the hair or skin may have particular elements or compounds. The hyper-spectral imaging analysis may be implemented to provide information about the hair and skin color, but also provides further information as to what may be exhibiting the color. Similar or identical colors may be formed from vastly different compounds, or, in other words, a variety of different compositions and/or elements may be responsible for providing a color spectrum when viewed in reference to visible light that looks the same. When treated, however, hair or skin that is the same color (on a color spectrum), may take treatments differently, and exhibit different results and effects. The hyper-spectral imaging component is configured to provide information about the constituents of the hair and skin. The information from the hyper-spectral evaluation and analysis may be used to generate a formulation profile for reaching a target for the hair or skin of the individual. One or more spectral profile libraries may be stored and the processor may be instructed with software containing instructions to implement a comparison and/or recognition routine to identify from the spectral information, certain chemicals, elements, compounds or other substances. The hair or skin compositions may be considered in conjunction with the hair image color spectra from the digital or first image camera.

According to some embodiments, the hyper-spectral imaging component is operated in conjunction with a dispensing system. The information provided from the hyper-spectral imaging of the hair and or skin may be used to determine the formulation for a desired target hair or skin treatment or application. For example, the imaging system may be operated to determine whether a user's hair or skin has been treated. A treatment chemical may be present on the hair. For example, an individual with dark hair may exhibit a dark brown color, but that may be due to dye placed on the hair, and the hair may be naturally gray. Another individual may exhibit the same or similar dark brown color, but it may be a natural color that is not dyed. Chemical components of dyes, hair colorants and other compositions are among a first level of substances that may be detected. Likewise, skin treatments and compositions also may be detected. According to some other embodiments, second level components, such as the components making up the individual's hair itself may be evaluated and determined. For example, the hair composition may include typical chemicals expected in healthy hair (or the hair of a healthy individual), but the hair composition also may include other chemicals, compounds or substances that may indicate an atypical condition or hair of an individual that may have a health disorder. The second level components may be elements or components of the hair composition itself. Minerals and elements may be associated with products applied to the hair, but, additionally, the hyper-spectral imaging component may ascertain information as to the makeup of the hair or skin. Components that are detected as forming the hair may include compositions or elements that indicate a beneficial or adverse health condition or exposure to a condition (environmental, dietary, or other). The devices, systems and methods provide information about the hair and skin, and may provide further information beyond what is on the hair and skin surface (i.e., beyond what is visible on the surface).

Figure 7A:
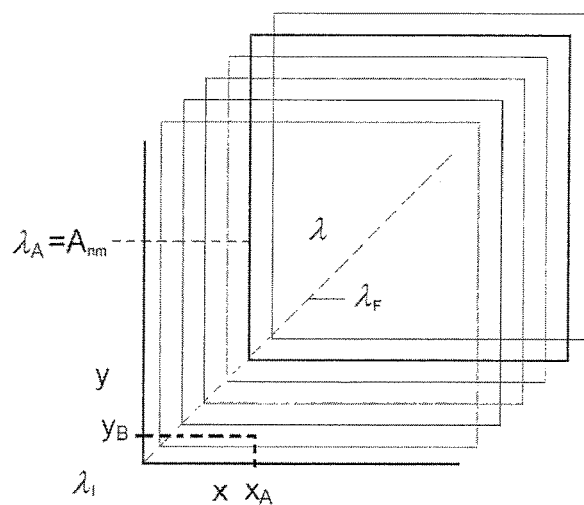
FIG. 7a is a schematic illustration representing a hyper-spectral imaging datacube and showing layers as a way to depict the cube.
Figure 7B:
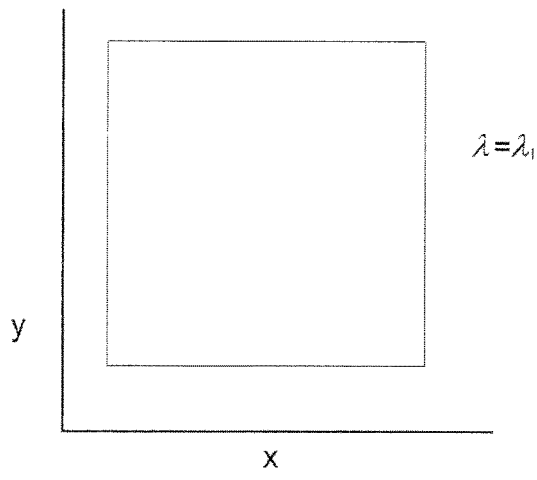
Figure 7C:
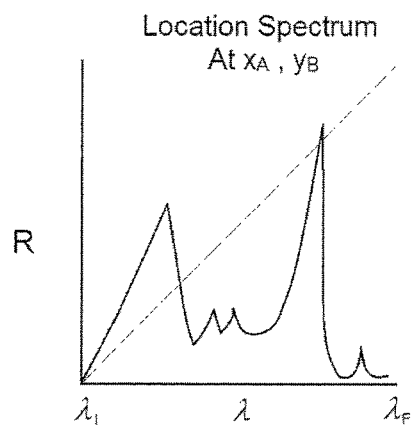

According to some preferred embodiments, a method for evaluating the hair and skin of an individual involves capturing a plurality of hyper-spectral images with the hyper-spectral imaging component 110 (or 110'). According to some preferred embodiments, a plurality of images are captured and are obtained as a 2-dimensional (2-D) sensor output that contains spatial (x,y) and spectral ($\lambda$) data. The hyper-spectral information may be represented in the form of a datacube, as illustrated in FIG. 6, wherein the (x,y,$\lambda$) coordinate structure defines a cube or datacube 210. The datacube 210 preferably provides a three-dimensional representation of the scanned wavelengths that are captured with the hyper-spectral imaging camera 110, 110'. According to some preferred embodiments, referring to FIGS. 7a and 7b, the datacube may be thought of as a stack of images, with each image acquired at a narrow spectral band. For example, as illustrated in FIG. 7a, a datacube is represented measuring a spatial location along the x and y axes and a wavelength dimension along the third or z axis, which is depicted as the X axis. The datacube is shown being represented by a plurality of image planes stacked on each other. Referring to FIG. 7b, an image plane ($\lambda_i$) is shown, as if it were removed from the cube, and represents the reflectance at the coordinate locations along the x-y axis for that wavelength ($\lambda_i$) for the subject imaged. The x-y axes preferably pinpoint a pixel plane P. The section of a point is expressed by $X_A, Y_B$, $\lambda_R = \lambda_I - \lambda_F$, where $\lambda_R$ represents a wavelength range, and where the range may be defined by $\lambda_I$, which is a starting wavelength of the wavelength range, and where $\lambda_F$ represents the wavelength at the end of the wavelength range. A point defined by the location of x,y, such as the point shown for example, $X_A, Y_B$, defines a spatial location which preferably represents a pixel, which represents a corresponding location of the imaged hair or skin. That point or pixel $X_A, Y_B$ location, may be represented in the datacube of the hyper-spectral imaging information to obtain and record wavelength and reflectance data. For example, the image location represented by location $X_A, Y_B$ (in this example), has a corresponding reflectance property or value at each respective wavelength or wavelength band measured by the hyper-spectral imaging component. The location of the spatial coordinate $X_A, Y_B$, corresponding to a location of the hair or skin of the individual, has an associated location spectrum. The location spectrum may be the reflectance value at the particular wavelength (or wavelength band). FIG. 7c illustrates an exemplary embodiment of a reflectance value plotted against the wavelength, and reflectance values for wavelengths at a spatial coordinate or pixel $X_A, X_B$. Therefore, referring to FIG. 7a, taking the point $X_A, Y_B$, along the $\lambda$ axis, the reflectance value is represented for each wavelength or wavelength band. Preferably, reflectance values at the pixel or spatial location $X_A, Y_B$ are obtained for adjacent wavelengths, throughout the wavelength range, such as, for example, the range $\lambda_I - \lambda_F$. A hyper-spectral cube may be generated from the hyper-spectral imaging of the individual's hair or skin (or both).

For example, the hyper-spectral image component includes a plurality of sensors, such as those sensors 120a, . . . represented in the exemplary embodiment of the hyper-spectral imaging component 110, which collect information. The collection of the information may be as a set of 'images'. According to some preferred embodiments, each of the images making up the image set represents a narrow wavelength range of the electromagnetic spectrum (or spectral band). The three-dimensional hyper-spectral datacube preferably is formed from the combined images. An example of the datacube is represented in FIG. 6. The datacube provides information that may be evaluated through analysis and processing to provide information about the individual whose hair or skin was imaged using the hyper-spectral imaging component. The imaging components of the hyper-spectral cameras are configured to measure 2D arrays. The detectors are configured to measure the wavelengths over the suitable wavelength ranges. The light source or filter, such as, for example, a tunable filter, provides reflectance for wavelengths, as the imaging takes place. The detector records and sends signals to the processing circuitry for processing and storage. Processing may involve comparison with hyper-spectral fingerprints of substances involved in the consideration for the product or formulation to be applied to the hair or skin. For example, if particular metal components are in dyes on the hair, the dye fingerprint may be ascertained through the hyper-spectral imaging of the hair by matching signatures of the dye, one or more metals or other molecules or substances (e.g., dye components), with the hyper-spectral image. The spectral cube for an individual's hair, for example, identifies the substance on the hair, and composition in the hair, and, in addition, the location at which the substances are found.

According to preferred embodiments, the hyper-spectral imaging is carried out to provide a hair map, which, in preferred embodiments, may be a hyper-spectral map of the entire hair or substantially most of the user's hair. For example, the hyper-spectral imaging component or camera may be configured to view the entire hair as a spectral cube.

This is done from an angle at which the camera image input is taken. In the case of skin, the hyper-spectral imaging component, such as the hyper-spectral camera, may view the person's entire face as a spectral cube. The spectral cube provides information across the wavelengths, which may be from 400 to 12,000 nm, and over the spatial dimension of the hair. Therefore, for example, where a user has hair that includes multiple treatments, such as, for example, highlight areas, and darker areas, the hyper-spectral imaging information may be utilized to identify the presence of the highlight and dark areas. In addition, the imaging information may be configured to provide locations of the areas and their respective conditions. Since a respective condition generally may exhibit visible spectral differences (observable with the visible image camera as in FIG. 1), the hyper-spectral imaging information may identify further distinctions of the hair at the imaged location, including at those visibly different locations, and at locations that may appear to be the same (in the visible spectral image). As discussed herein, one or more libraries may be provided with hyper-spectral data that corresponds with an element that may be detected in the hair. In the case of the hair formulation information, the library may contain information that corresponds to different hair treatments that are customarily applied to hair, such as bleach. A hyper-spectral library may be provided with hyper-spectral data (spectra) that correspond to the presence of bleach (or its components). When the hyper-spectral image data is obtained for a target individuals' hair, processing may include comparing the obtained data with the library to determine whether a match for a substance is present. In the case of an identification of the presence of a substance, such as, for example, bleach, the instructions or formulations may be adjusted or generated in conjunction with a desired result or target hair color or condition sought. Dyes also may be considered to determine whether the hyper-spectral profile of a target individual's hair (including any portion thereof), has a dye treatment on it. The library or libraries may be configured to include hyper-spectral profiles for various hair compositions and those compositions appearing on hair. For example, the system and method may evaluate the hyper-spectral information from the target user obtained from the hyper-spectral imaging component, and determine the presence of components, and provide a hair profile for the existing hair. The existing hair profile may include not only the visible image spectra, but components or treatments that are on the hair, and compositions that may be composing the hair. This hair profile facilitates providing a proper treatment, or enhancement to arrive at a proper target color or condition for the hair (e.g., a curl or wave, a different color, highlights, and the like). In accordance with embodiments of the invention, the user's skin also may be profiled to determine the presence of treatments. In addition, according to some other embodiments, the user's hair and skin may be profiled using the hyper-spectral imaging and data to determine potential health conditions. In the event that a treatment to be applied to hair or skin is contradicted based on the presence of a medication, compound or other condition, the system may be provided with information that provides the compatibility or incompatibility warning when the hyper-spectral profile is determined to match a contrary profile. The detection may be made without a specific substance being identified, as a measure of preserving privacy.

According to some embodiments, information may be stored in many various manners so as to make information about the user's hair or skin available to the user and others designated to view it, and to prevent association of a single user with the user's personal profile information should the information fall into the wrong hands. For example, user data may be stored separately from identifiable user information, and concatenated as needed. In addition, other security measures, such as, for example, encryption of the information, and its transmission, may be implemented in connection with storage and transporting the data.

Although the figures show separate cameras, the imaging or first camera and the hyper-spectral camera or cameras may be provided to image the individual while the individual is seated at the same location or position. The positioning of the first camera in FIG. 1, and the hyper-spectral cameras in FIGS. 2 and 3, preferably are shown is separate depictions for purposes of illustrating the invention, but may be provided together, as in the environment if FIG. 1 or any of FIGS. 2 and 3. In addition, a plurality of light sources, or alternative light sources that may be controlled to provide light at the desired wavelengths or energy levels for the visible imaging of the first camera, and the hyper-spectral imaging of the hyper-spectral imaging component or camera. According to some embodiments, the hyper-spectral imaging component may image light having wavelengths that include the visible light spectrum. Narrowband or broadband lighting sources may be used to provide illumination to the subject, such as, the individual's hair and skin.

Band pass filters may be electronically controlled to be positioned and/or removed from the light path, so that a plurality of images for wavelengths of light passing through may be obtained. A remotely associated computing device, such as a server, may control, or be manipulated to control the band, wavelengths, or substance to detect.

A calibration mechanism preferably is provided and used to provide uniformity among the information obtained. The calibration mechanism preferably includes a calibration component that is positioned on the individual, or at the location where the individual's hair or skin will be when imaged. According to one exemplary embodiment, the calibration component comprises an element having a highly reflective surface. The element preferably has a uniform surface, and the calibration component may be illuminated with radiation from a radiation source, and the reflectance calculated to provide a reference calibration value (RCV). A dark reference value (DRV) also is obtained in conjunction with the calibration. The DRV may be obtained by covering the lens or opening of the hyper-spectral imaging component, turning off or dimming the illumination source, and recording the hyper spectral imaging response on the detector of the hyper-spectral imaging component. The reference calibration value (RCV) and dark reference value (DRV) may be obtained before each imaging of a subject, or alternatively, may be done at some other period of frequency, such as, for example, once per day. The reference values preferably are stored for subsequent readings. According to some preferred embodiments, the hyper-spectral imaging data obtained for an individual's hair and skin preferably are determined by providing an adjusted data set, where a hyper-spectral imaging reference point is obtained at the location (x,y) and for a wavelength ($\lambda$), calibrated with reference to the RCV and DRV values. According to some embodiments, the hyper-spectral image value (HSIV) is adjusted or calibrated using the calibration mechanism and the calibration values obtained. The detector responses for the RCV and DRV may be utilized to calibrate readings. The HSIV may be obtained by dividing (a) the difference between the response value for the imaged hair (or skin) ($RV_H$) and the DRV by (b) the difference between the RCV and the DRV. For example, according to some embodiments, the calibration component is used to determine the RCV, and the image values for the hair and skin may be calibrated as follows:

$$HSIV=(RV_H-DRV)/(RCV-DRV)$$

The calibration mechanism may be implemented as part of the data collection and processing, and may be done by one or more processing components, including processing components provided on or in association with the hyper-spectral imaging component. The calibration mechanism also may be configured with range limitations for alerting when a condition is beyond a calibration level parameter (e.g., when light intensity falls off, indicating a potentially failing or problem with a light source, or when the detector of the hyper-spectral imaging component is providing extreme readings). The hyper-spectral imaging value (HSIV), according to preferred embodiments, may be a value of reflectance (at a designated wavelength or wavelength band). Alternative embodiments, may consider other electromagnetic radiation effects, such as, for example, transmittance, absorbance, emission, luminescence.

A proposed example of the system is provided.

Example 1

An individual arrives at a salon location for a hair treatment. The face and hair of the individual is imaged using a standard digital camera, such as the camera illustrated in FIG. 2. This records the current look of the individual. The image is stored. A plurality of images may be taken. The individual's hair is washed and dried. The individual is then imaged with the hyper-spectral imaging components, such as the camera illustrated in FIG. 3. The individual has medium tone brown hair with red. A lighting source that emits electromagnetic radiation throughout a spectrum of from about 400 nm to about 12000 nm is operated. The lighting source may comprise a single or multiple lights, including halogen, a laser or other suitable electromagnetic radiation source. In this example, wavelengths covered are emitted in bands of 20 nm, over the range of about 800 nm, providing imaging date in the form of a spectral cube with 40 wavelength image layers for an imaged location (x, y coordinates on an imaging plane). In addition, the hyper spectral imaging camera is moved to image four different locations, so as to provide imaging views and information for the individual's hair on top, back, and each side. The imaging data is recorded by the detector, which, in this example is a component of the hyper-spectral camera and comprises an array of detector cells forming the image plane (defined in x,y coordinates). The image information is processed and evaluated by comparison of the imaging information, which may be the hyperspectral datacube, to determine whether there is a match with a spectral fingerprint. The system preferably has a hair substance fingerprint database. Hyper-spectral profiles for substances on the hair are included, such as, for example, dyes and bleaches. Hair treatment product profiles may comprise a first set of fingerprints. In addition, the hair profile database may include a second set of fingerprints, which are the compositions making up the hair. In this example, the individual's hair is imaged and a mineral is found in the hair (e.g., chromium). The hyper-spectral imaging may also determine the strength or intensity of the image response. In this example, the chromium response was relatively strong. The individual may be advised of certain results. For example, where the hyper-spectral imaging indicates the presence of certain metals, minerals or other substances, the individual may be advised to visit a physician or nutritionist.

Figure 9:
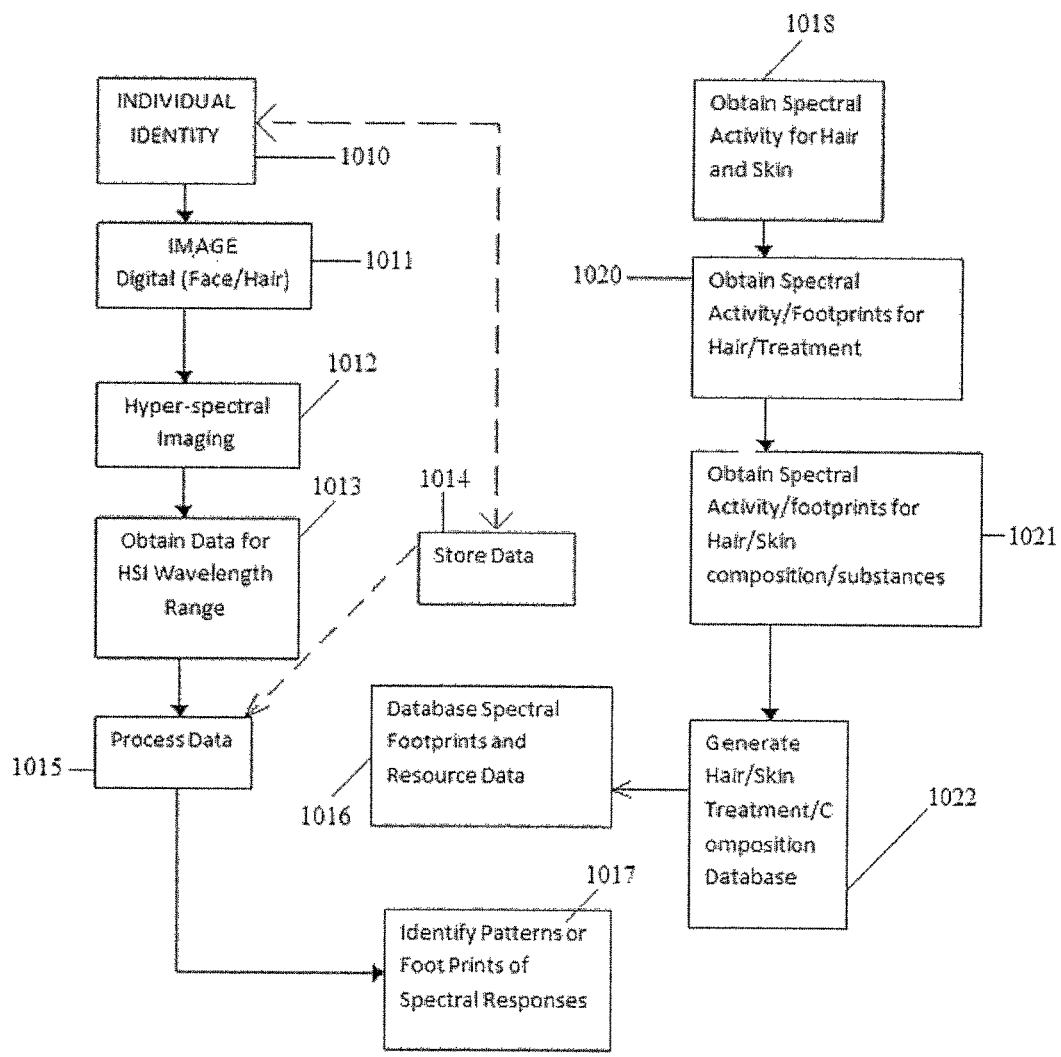
FIG. 9 is a flow diagram of an exemplary embodiment of a method for implementing hyper-spectral imaging analysis in conjunction with providing a hair or skin treatment.
Figure 10:
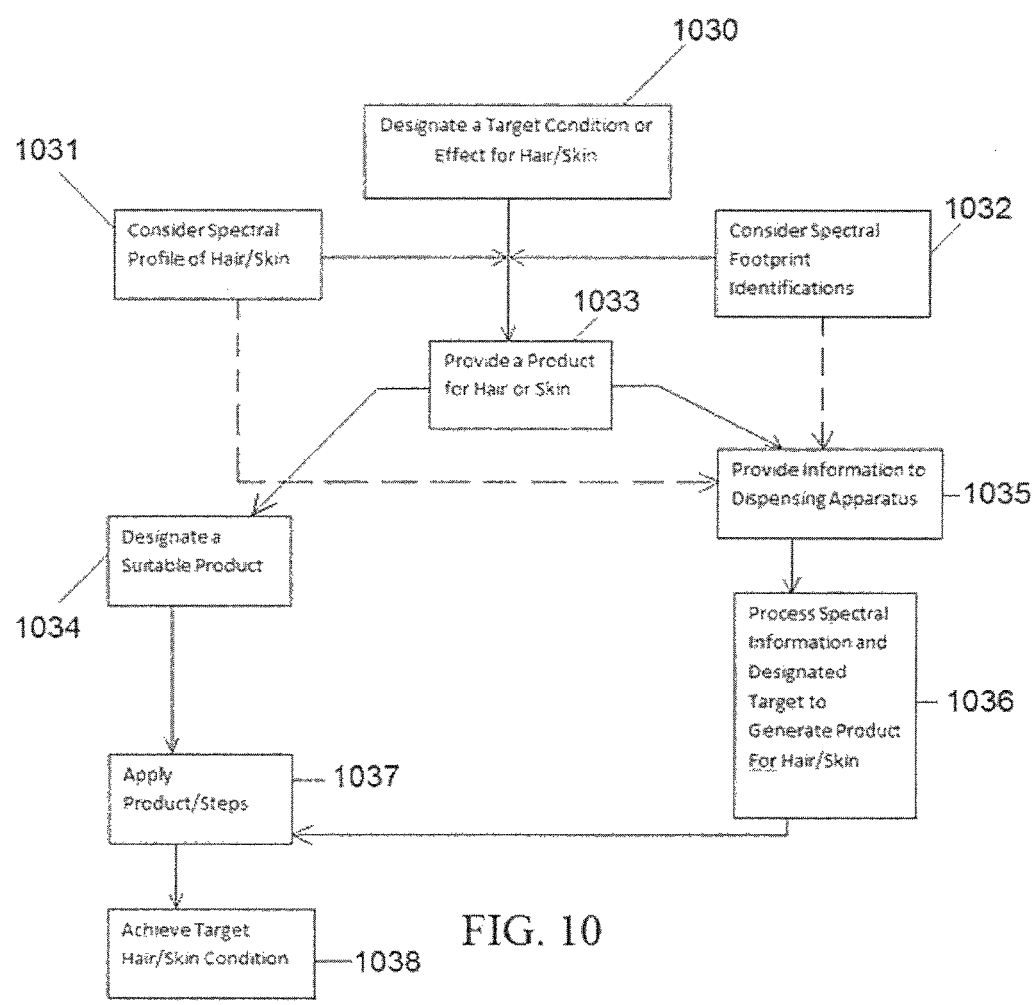
FIG. 10 is a flow diagram illustrating the further implementation of the method steps of FIG. 9 to provide a treatment to achieve a target hair or skin result.

Referring to FIGS. 9 and 10, an exemplary illustration of the system is provided. An individual identity or profile 1010 is shown. This may be accomplished by an individual or salon personnel inputting information about the individual, which may be contact information, payment information, preferences, age, hair color, eye color, skin type and other information that may be useful for determining hair or skin. Alternate embodiments may optionally include additional information, such as allergies, medications, and other health related information. The individual may optionally input the additional health information in a privacy screen, and may opt not to share that with any personnel. For example, the information may be stored to be active as it may pertain to a treatment or condition, or product, but may not be visible to salon personnel. In instances where the condition prevents a particular reaching of a target condition or treatment, the system device may indicate the lack of a solution only, to indicate to the salon personnel not to proceed. Accordingly, an alternative product or treatment may be indicated. A digital image 1011 of the individual, preferably the head and face (hair and skin) is taken and stored. A hyper-spectral image is obtained by hyper-spectral imaging 1012 using a hyper-spectral imaging component, such as, for example, the hyper-spectral cameras 110,110' shown and described herein. The electromagnetic radiation is directed to the hair and skin and reflected off of the hair and skin. The image capture provides data that is obtained from the individual's hair or skin 1013. The capture of the image, which, for example, may be reflected electromagnetic radiation (reflected from the hair or skin), is obtained and recorded for a wavelength range, and may be done for adjacent wavelength bands. The hyper-spectral imaging data preferably is stored 1014, and may be stored in conjunction with the individual identity data or profile 1010. The hyper-spectral information is processed 1015 to provide the wavelength response at the various pixel or spatial locations (e.g., x,y coordinates). Processing the hyper-spectral information may include determining and recording the detector response to reflected electromagnetic radiation at different wavelengths. The hair and skin may exhibit reflectance profiles that are unique to different locations of the hair and skin, and for different wavelengths.

According to a preferred embodiment, a hyper spectral database 1016 is provided to make available resource data, such as, a fingerprint profile for hair compositions and substances that may compose the hair (e.g., chromium, chlorine, etc.) and for compositions that may be present on the hair (e.g., dyes, bleaches, etc.). The hyperspectral data obtained for an individual's hair or face 1013 is processed 1015. The processing may include comparison of the data to the database 1016 profiles. The processing preferably identifies one or more fingerprints, which identify substances present on or in the hair or skin 1017. According to preferred embodiments, the database of spectral resource data 1016 is generated by obtaining hyper-spectral activity profiles for hair and skin 1018. The hyper-spectral activity profiles are responses of components in the hair or skin or treatments to particular wavelengths or hyper-spectral activity. The spectral footprints are obtained for hair treatments that may be present on hair, such as dyes used to color the hair, bleaches, and other chemicals 1020. According to preferred embodiments, the hyper-spectral footprint data for hair treatments preferably are obtained through imaging hair with a known hair component. Construction of a library or database 1022 may be accomplished to provide a reference database 1016 of hair treatment compositions, including dyes, such as, different color dyes, dyes from different manufacturers, and other treatment chemicals and brands that may be used. A library may be stored in a database 1016 that is referenced when performing a hyper-spectral imaging and analysis of hair or skin of an individual (1010-1017). In addition to imaging and collecting information about potential treatments that have been applied to hair or skin 1020 for the database 1016, the system, method and devices preferably, may image and collect information about components making up the hair 1021. A database of hair treatment compositions and components that make up the hair is generated 1022. Compositions and substances that make up the hair or skin, or that have historically found their way into the hair or skin may be imaged and stored in a reference library or database, such as the database of spectral footprints and resource data 1016. The database 1016 may be updated as conditions change, such as, for example environmental conditions, to provide a broader range of detectable substances.

In some cases, for example, the hyper-spectral imaging may identify a strong value for a particular wavelength, or for a plurality of wavelength bands (which may not necessarily be adjacent bands, see, e.g., FIG. 7c). For example, the hyper-spectral information may locate the presence of a particular substance, e.g., selenium, as a component of the hair or skin, and may locate the regions or spatial locations of the hair and skin where the substance is present. According to some embodiments, the presence may be quantified relative to other areas of the skin or hair. The identification of treatment that has been applied to the hair or skin, and substances that compose the hair (or skin) is provided based on the hyper-spectral imaging of the hair or skin, and the information collected. The substances and treatments preferably may be identified based on the hyper-spectral activity, preferably, reflectance activity. The identification of the substances and treatments may be used for selection and generation of custom products and formulations for hair and skin. Referring to FIG. 10, an exemplary illustration of a schematic diagram where, according to this example, an individual is having a treatment on the skin or hair in order to reach a target effect. The target condition for the hair or skin is designated 1030. This may be done utilizing the individual identity information 1010 and digital imaging information 1011, and the stored data 1014, which may include profile data of the individual, including hair and skin information. The target effect or condition of the hair or skin that the individual desires may be selected or designated in accordance with any method, and, according to a preferred method, may be selected or designated using the devices and tools disclosed in Colorculture Network, LLC's U.S. Pat. No. 8,977,389. The target, for example, may be a color that the individual seeks the hair to have. In this example, the target may be a dark brown hair color. The individual has light brown hair in the digital image 1011 (and if viewed in person, as an observable characteristic). The hyper-spectral imaging 1012 is carried out, and the hyper-spectral profile of the hair is obtained 1013, processed 1015. Patterns, such as footprints, are identified. 1017. The target, which here is dark brown, requires a treatment of the hair to take it from its current light brown color to the dark brown color target. The treatment may be a dye. However, in the present example, the hyper spectral imaging identifies a footprint of hair dye present on the individual's hair. In addition, the hyper-spectral imaging identifies compositions that correspond with gray hair. Therefore, the spectral footprint identifications of a hair treatment present on the hair, and gray hair as an underlying condition or status, are considered 1032. The consideration of the hair conditions (in this example, the treatment and gray hair status) are utilized in conjunction with providing a product for the hair 1033 to produce the target hair color 1038, which, in this example, is dark brown. The product, according to some embodiments, is provided 1034 based on the identification of the present hair conditions and desired target. According to some preferred embodiments, a product is generated using a dispensing apparatus to produce a suitable product that when applied will accomplish the desired target look 1035 (e.g., dark brown). The dispensing apparatus 1035 or other suitable processing component (whether provided on, in association with, or linked for communication with the dispensing apparatus) processes the spectral information, including the footprint information, and considers the information in view of the designated target 1036. The product may be formulated through a number of components. The components, including the type of component, and component amount, are manipulated and adjusted based on the hyper-spectral imaging information 1031, 1032. Step 1036 is identified and may take place entirely, or partially at the dispensing apparatus. For example, the generation of the product may be the only step that takes place at the dispensing apparatus, while in other embodiments, one or more evaluation or processing steps may take place at the dispensing apparatus. Once a product is provided 1033, 1034 or generated 1036, the product is applied to the hair using the appropriate procedures for its application 1037 (e.g., brushing on, spraying, sponging, encasing for light omission, etc.) The hyper-spectral imaging data collection and evaluation of the information provides the appropriate information about the hair or skin.

According to some preferred embodiments, the hyper-spectral information may be profiled according to database information, such as resource data and footprints. The profiling of the information may be done by storing one or more hyperspectral imaging collected data with a corresponding formulation adjustment or correction (FA), in regard to the formulation effect (FE). For example, if a product formulation effect (FE) is to produce a red hair tone, then the hyper-spectral profile (HSP) may be created for that product, and the formulation effect (FE) may be considered in regard to the hyper-spectral information data (or range) parameters. For example, where the hyper-spectral information provides an indication of the presence of prior treatments on the individual's hair (or skin), the prior treatments may be considered in making a formula adjustment (FA) so as to provide a formula that, when applied to the (hair or skin) will achieve the target effect or condition. According to preferred embodiments, a database or library of hyper-spectral imaging information in regard to potential formulations or adjustments to formulations, may be generated, and stored. The database may provide a reference for the hyper-spectral information collected for an individual desiring a particular target, and may provide information for selecting or generating the appropriate product to be applied to the hair. The hyper-spectral database, additionally, or alternatively, may be provided with recommended steps, in the event that a step (time, washing, pretreating, encasing), is required. The database preferably may be generated or created based on components of hair, hair type, or hair treatment substances that have been applied to hair. The hyper-spectral database or profile also may include information relating to hair (or skin) composition, that is, which may include substances that compose the hair (or skin). Where one or more substances composes the hair (or skin) has an effect on reaching the target, then that hyper-spectral information may be used to provide the database.

According to a preferred embodiment, a formulation effect (FE) may be designated for hyper-spectral imaging footprints that are obtained for hair or skin, in connection with a particular product. For example, a footprint that identifies chromium in the hair may generate an instruction to provide a formulation adjustment (FA) to an amount of a formula component, or an addition of a component. The formulation adjustment (FA) may be made to an existing product, existing formula, or product being produced from a dispensing apparatus. Adjustments may be made based on prior treatments identified as being present on the hair (or skin) as well as component substances composing the hair.

Example 2

Example 2 is similar to Example 1, above, except that the person's hair is evaluated using the hyper-spectral imaging camera, and the hyper-spectral imaging data for the individual's hair identifies a profile that corresponds with the absence of the outer protective coating usually found on the hair fibers. The system identifies the hair as being previously bleached or lightened. The formulation therefore is adjusted to provide a compatible product that may be used to achieve the target on the hair presented.

Example 3

Example 3 is similar to Example 2, above, however, the product to apply to produce the target is not compatible with the individual's hair. In this situation alternative options are explored. The individual is presented with a time frame for providing the appropriate target look (which may require a delay of days or weeks), or alternatively, another option that involves a compatible color product.

The hyper-spectral profile (HSP) may provide an overall spectral profile as well as areas of increased or decreased response, which typically appear as peaks or valleys when the reflectance (at a spatial location or pixel) is considered against the wavelength (as in FIG. 7c). Though not illustrated in that figure, the presence of certain components or substances may exhibit notably increased or decreased responses (which in FIG. 7c would appear as strong peaks or valleys) as a response at certain wavelengths. The hyper-spectral profile preferably may record these responses and identify substances present on or components composing the hair or skin by an overall hyper-spectral profile (for example, at the wavelengths or wavelength bands imaged), as well as particular areas at specific wavelengths where a narrow abrupt change is identified (e.g., a strong peak or valley). The identification may be carried out by processing the hyper-spectral image information with a processor, and using software containing instructions to compare the imaged information with spectral profile data. The hyper-spectral profile data may include a footprint that includes a spectral curve corresponding with a particular condition or component relating to the hair or skin hyper-spectral image analysis, and may also include as part of the footprint one or more specific response profiles (such as an increased response or peak) at one or more particular wavelengths or wavelength bands.

The input for information obtained in connection with the individual identity may, for example, include a digital image of the individual, preferably the hair ad face. According to preferred embodiments, the image is obtained using a digital camera, such as the camera 102 shown and described herein. The digital camera 102 preferably is utilized as a single camera, or with multiple cameras, to record the image of the individual (e.g., head and face). In some embodiments, the camera or cameras are mounted to be in a position or to move in order to capture the head and hair from a 360 degree view (e.g., front, sides and back). In this manner, the image spatial locations may be processed, stored and displayed to correspond with the hyper-spectral image coordinates (e.g., x-y, coordinates or pixels). Although the camera 102 is shown and referred to, according to some alternate embodiments, the individual image may be captured using any suitable capture device, such as, for example, a camera of a PDA, phone, tablet or other suitable imaging component.

While the invention has been described with reference to specific embodiments, the description is illustrative and is not to be construed as limiting the scope of the invention. Although preferred embodiments illustrating a hyper-spectral imaging component as a camera 110,110',310,410 are shown, the hyper-spectral imaging component may include alternate configurations, other than the depiction illustrated in FIG. 4. Various modifications and changes may occur to those skilled in the art without departing from the spirit and scope of the invention described herein and as defined by the appended claims.

What is claimed is:

1. A system for determining one or more products or product formulas for application to the hair or skin of an individual, comprising:
   a) a hyper-spectral imaging component that generates a series of wavelengths that respond to an element or substance that is indicative of its presence in the hair or skin;
   b) a hyper-spectral library that contains hyper-spectral data that corresponds to the presence of elements or substances in the hair or skin;
   c) a processing component configured with software containing instructions to process information from said hyper-spectral imaging component and identify a first condition of said hair or skin, wherein said information comprises a hyper-spectral footprint, and wherein said first condition is the presence of said element or substance identified by the comparison of the hyperspectral footprint to the hyper-spectral library;
   d) software containing instructions to receive an input of a target for said hair or skin; and
   e) wherein said processing component is configured with instructions to select said one or more products or product formulas, or adjust said one or more products or product formula for the said one or more products that when applied to said hair or skin having the identified first condition provides the target taking into account of or in the presence of the indicated element or substance; and
   f) selected said one or more products or product formulas, or adjust said one or more products or product formula for the said one or more products that when applied to said hair or skin provides the target.

2. The system of claim 1, including a dispensing apparatus, and wherein said product is provided by said dispensing apparatus.

3. The system of claim 2, wherein said dispensing apparatus includes a plurality of component products which are dispensed to provide said product.

4. The system of claim 1, wherein said hyper-spectral imaging component comprises a 2D array of sensors.

5. The system of claim 4, wherein said hyperspectral imaging component is configured to take a plurality of images of said hair or skin.

6. The system of claim 5, wherein said images are stored and comprise a spatial component and a wavelength component.

7. The system of claim 6, wherein said spatial component is an x,y coordinate and where said wavelength coordinate is the wavelength.

8. The system of claim 7, wherein said system generates a hyper-spectral cube, and wherein said hyper-spectral imaging component captures images that provide information to generate the hyper-spectral cube.

9. The system of claim 8, wherein said information generating said hyper-spectral cube is processed to provide an indication of substances present on said hair or skin of the individual.

10. The system of claim 9, wherein said indication of substances includes prior hair or skin treatments.

11. The system of claim 10, wherein said prior hair or skin treatments are identified, and wherein said product is selected based on said identified prior treatment.

12. The system of claim 11, wherein said prior treatment is a hair dye, and wherein said product is a hair dye.

13. The system of claim 12, further including an electromagnetic radiation source for illuminating said hair or skin.

14. The system of claim 13, wherein said electromagnetic radiation source comprises a light source.

15. The system of claim 14, wherein said light source comprises a broadband light source.

16. The system of claim 15, wherein said broadband light source is provided on a track or in-line with said hyperspectral imaging component.

17. The system of claim 14, wherein said light source comprises a tuned laser, configured to shine a specific wavelength onto said hair or skin, and wherein said hyperspectral imaging component is synchronized with said tuned laser to measure the wavelength being illuminated from said laser, and wherein said laser is swept in wavelength to provide a range of wavelengths.

18. The system of claim 17, wherein said laser wavelengths are generated throughout a range of from 400 to 12000 nanometers.

19. The system of claim 13, wherein said electromagnetic radiation source illuminates at wavelengths from about 400 to about 12000 nanometers.

20. The system of claim 12, further including a calibration component.

21. The system of claim 20, wherein said calibration component comprises a swatch that provides a known spectral response.

22. The system of claim 21, wherein said swatch is positionable on said hair or skin.

23. The system of claim 21, wherein said calibration component comprises an element with a reflective surface.

24. The system of claim 1, further including a calibration component.

25. The system of claim 1, wherein said processing component configured with software containing instructions to process information from said hyper-spectral imaging component and identify a condition of said hair or skin, includes instructions for generating a hyperspectral profile of said hair or skin with said hyperspectral imaging component.

26. The system of claim 25, wherein said library comprises a library of hyperspectral footprints to match the hyperspectral footprints of a substance in order to detect whether a substance is present on or in the hair imaged by the system.

27. A method for providing a treatment to the hair or skin of an individual comprising:
a) providing a hyper-spectral imaging component that generates a series of wavelengths that respond to an element or substance that is indicative of its presence in the hair or skin;
b) providing a hyper-spectral library that contains hyper-spectral data that corresponds to the profiles of elements or substances in the hair or skin;
c) emitting via an electromagnetic radiation source electromagnetic radiation at the hair or skin of the individual, said electromagnetic radiation being emitted over a range of wavelengths;
d) imaging the hair or skin of said individual with said hyper-spectral imaging component, the hyper-spectral imaging component producing detection signals, said detection signals comprising detector responses to electromagnetic radiation of a wavelength or wavelength band and a corresponding spatial coordinate location; and recording the detection signals detected;
e) processing the detector responses with a hardware processing component to compare the detector responses with the hyper-spectral data profiles of said elements or substances in the hyper-spectral library, wherein the detector responses are processed to generate one or more hyper-spectral footprints;
f) determining a condition of the hair or skin for which a treatment is to be applied, wherein said condition is a presence of said element or substance identified by the comparison of the generated one or more hyper-spectral footprint to the hyper-spectral library;
g) assigning a target for said hair or skin in response to the condition determined in step f); and
h) providing one or more treatment products or protocols that will produce the assigned target.

28. The method of claim 27, wherein said detector responses comprise a hyper-spectral datacube.

29. The method of claim 27, including dispensing said product from a dispensing apparatus.

30. The method of claim 29, wherein dispensing comprises dispensing a plurality of product components and forming a product comprising said dispensed product components.

31. The method of claim 27, including calibrating said hyper-spectral imaging component.

32. The method of claim 31, wherein calibrating comprises imaging a calibration component of known reflectance, obtaining the detector responses from the reflection of electromagnetic radiation from said calibration component, and comparing the known calibration component reflectance with the detector responses from the reflection of electromagnetic radiation from said calibration component to obtain a calibration factor.

33. The method of claim 32, including adjusting the detection response to electromagnetic radiation detected from the reflection of the hair or skin by applying the calibration factor.

34. The method of claim 33, wherein applying the calibration factor comprises: dividing (a) the difference between the response value for the imaged hair or skin ($RV_H$) and the dark reference value (DRV) by (b) the difference between the reference calibration value (RCV) and the dark reference value (DRV).

* * * * *